United States Patent
Roth et al.

(10) Patent No.: US 7,393,696 B2
(45) Date of Patent: Jul. 1, 2008

(54) BOVINE PREGNANCY TEST

(75) Inventors: Jay W. Roth, Colorado Springs, CO (US); Mark Colgin, Castle Rock, CO (US); Roger Hurst, Castle Rock, CO (US); Diane Newman, Littleton, CO (US); Cathy Landmann, Highlands Ranch, CO (US)

(73) Assignee: AspenBio Pharma, Inc., Castle Rock, CO (US)

(*) Notice: Subject to any disclaimer, the term of this patent is extended or adjusted under 35 U.S.C. 154(b) by 979 days.

(21) Appl. No.: 10/255,162

(22) Filed: Sep. 24, 2002

(65) Prior Publication Data

US 2003/0073248 A1 Apr. 17, 2003

Related U.S. Application Data

(60) Provisional application No. 60/380,042, filed on May 2, 2002, provisional application No. 60/377,829, filed on May 2, 2002, provisional application No. 60/377,355, filed on May 2, 2002, provisional application No. 60/377,165, filed on May 2, 2002, provisional application No. 60/377,921, filed on May 2, 2002, provisional application No. 60/380,043, filed on May 2, 2002, provisional application No. 60/377,166, filed on May 2, 2002, provisional application No. 60/377,987, filed on May 2, 2002, provisional application No. 60/337,871, filed on Nov. 8, 2001, provisional application No. 60/325,663, filed on Sep. 28, 2001.

(51) Int. Cl.
*G01N 33/53* (2006.01)

(52) U.S. Cl. .............. 436/510; 436/514; 436/518; 436/524; 436/530; 436/531; 436/161; 436/164; 436/63; 436/65; 435/287.1; 435/287.2

(58) Field of Classification Search ................ 436/518, 436/524, 530, 531, 161, 164, 63, 65; 435/7.21, 435/287.1, 287.2
See application file for complete search history.

(56) References Cited

U.S. PATENT DOCUMENTS

| | | | | |
|---|---|---|---|---|
| 3,817,837 A | 6/1974 | Benz | ............................ | 162/113 |
| 3,850,752 A | 11/1974 | Wilhelmus | ............ | 195/103.5 R |
| 3,892,855 A | 7/1975 | Short | .......................... | 424/238 |
| 3,939,350 A | 2/1976 | Kronick et al. | .............. | 250/365 |
| 3,996,345 A | 12/1976 | Ullman et al. | ................. | 424/12 |
| 4,275,149 A | 6/1981 | Litman et al. | ................... | 435/7 |
| 4,277,437 A | 7/1981 | Maggio | ........................ | 422/61 |

(Continued)

FOREIGN PATENT DOCUMENTS

EP 0 132 750 2/1985

(Continued)

OTHER PUBLICATIONS

Ahrens, P.B. et al., "Tumour necrosis factor enhances induction by β-interferon of a ubiquitin cross-reactive protein," (1990) *J. Gen. Virology* 71:1675-1682.

(Continued)

*Primary Examiner*—Bao-Thuy L. Nguyen
(74) *Attorney, Agent, or Firm*—Greenlee Winner and Sullivan PC

(57) ABSTRACT

This invention provides bovine pregnancy test methods and devices. The test is also suitable for other ruminant and/or ungulate animals. Antigens from Group A (early pregnancy antigens), and/or Group B (mid-pregnancy antigens), and Group C (early, mid- and late pregnancy antigens) are detected in a fluid from the animal, and pregnancy is reliably determined. The pregnancy assays of this invention are preferably carried out using immunoassay devices which provide immediate results in the field.

11 Claims, 6 Drawing Sheets

U.S. PATENT DOCUMENTS

| | | | |
|---|---|---|---|
| 4,313,734 A | 2/1982 | Leuvering | 23/230 B |
| 4,366,241 A | 12/1982 | Tom et al. | 435/7 |
| 4,376,110 A | 3/1983 | David et al. | 436/513 |
| 4,435,504 A | 3/1984 | Zuk et al. | 435/7 |
| 4,486,530 A | 12/1984 | David et al. | 435/7 |
| 4,518,565 A * | 5/1985 | Boger et al. | 422/58 |
| 4,554,256 A | 11/1985 | Sasser et al. | 436/510 |
| 4,610,687 A | 9/1986 | Fogwell | 604/891 |
| 4,668,621 A | 5/1987 | Doellgast | 435/13 |
| 4,703,017 A | 10/1987 | Campbell et al. | 436/501 |
| 4,705,748 A | 11/1987 | Sasser et al. | 435/7 |
| 4,740,468 A | 4/1988 | Weng et al. | 435/7 |
| 4,755,460 A | 7/1988 | Bostwick et al. | 435/7 |
| 4,855,240 A | 8/1989 | Rosenstein et al. | 436/514 |
| 4,877,742 A | 10/1989 | Maly et al. | 436/65 |
| 4,895,804 A | 1/1990 | Bostwick et al. | 435/240.27 |
| 4,954,452 A | 9/1990 | Yost et al. | 436/524 |
| 5,008,080 A * | 4/1991 | Brown et al. | 422/56 |
| 5,028,535 A | 7/1991 | Buechler et al. | 435/7.1 |
| 5,075,078 A | 12/1991 | Osikowicz et al. | 422/56 |
| 5,137,808 A | 8/1992 | Ullman et al. | 435/7.9 |
| 5,149,622 A * | 9/1992 | Brown et al. | 435/5 |
| 5,229,073 A | 7/1993 | Luo et al. | 422/56 |
| 5,360,895 A | 11/1994 | Hainfeld et al. | 530/391.5 |
| 5,589,457 A | 12/1996 | Wiltbank et al. | 514/12 |
| 5,591,645 A | 1/1997 | Rosenstein | 436/514 |
| 5,654,162 A | 8/1997 | Guire et al. | 435/7.92 |
| 5,739,290 A | 4/1998 | Horisberger et al. | 530/388.2 |
| 5,798,273 A | 8/1998 | Shuler et al. | 436/514 |
| 5,869,264 A | 2/1999 | Horisberger et al. | 435/7.1 |
| 6,180,102 B1 | 1/2001 | Hanai et al. | 424/152.1 |
| 6,248,598 B1 * | 6/2001 | Bogema | 436/518 |
| 6,352,861 B1 | 3/2002 | Copeland et al. | 436/510 |
| 6,406,922 B2 * | 6/2002 | Casterlin et al. | 436/518 |
| 6,869,770 B1 * | 3/2005 | Roberts et al. | 435/7.1 |
| 6,924,153 B1 * | 8/2005 | Boehringer et al. | 436/514 |
| 2001/0041697 A1 | 11/2001 | Foster et al. | 514/171 |
| 2002/0192838 A1 | 12/2002 | Ott | 436/510 |
| 2003/0143601 A1 | 7/2003 | Hansen et al. | 435/6 |

FOREIGN PATENT DOCUMENTS

| | | |
|---|---|---|
| EP | 0 725 081 | 8/1996 |
| EP | 0 810 436 | 12/1997 |
| WO | 88/08534 | * 11/1988 |
| WO | WO 88/08534 | 11/1988 |
| WO | WO 94/12537 | 6/1994 |
| WO | WO 95/16207 | 1/1995 |
| WO | WO 99/47934 | 9/1999 |
| WO | WO 00/51520 | 9/2000 |
| WO | WO 02/04006 | 1/2002 |
| WO | WO 02/103352 | 6/2002 |

OTHER PUBLICATIONS

Austin, K.J. et al., "Ubiquitin cross-reactive protein is released by the bovine uterus in response to interferon during early pregnancy," (1996) *Biol. Reprod.* 54:600-606.

Austin, K.J. et al. "Pregnancy-specific protein B induces release of an alpha chemokine in bovine endometrium," (1999) *Endocrinology* 140(1):542-545.

Austin, K.J. et al., "Complementary deoxyribonucleic acid sequence encoding bovine ubiquitin cross-reactive protein," (1996) *Endocrine* 5(2):191-197.

Baboshina, O.V., "Novel multiubiquitin chain linkages catalyzed by the conjugating enzymes ESEPF and RAD6 are recognized by 26 S proteasome subunit 5," (1996) *J. Biol. Chem.* 271:2823-2831.

Bebington, C. et al., "Localization of ubiquitin and ubiquitin cross-reactive protein in human and baboon endometrium and decidua during the menstrual cycle and early pregnancy," (1999) *Biol. Reprod.* 60:920-928.

Bebington, C. et al., "Ubiquitin cross-reactive protein gene expression is increased in decidualized endometrial stromal cells at the initiation of pregnancy," (1999) *Mol. Human Reprod.* 5(10):966-972.

Binelli, M. et al. "Antiluteolytic Strategies to Improve Fertility in Cattle," (Dec. 2001) *Theriogenology* 56(9):1451-1463.

Binelli M. et al. "Bovine interferon-tau stimulates the Janus kinase-signal transducer and activator of transcription pathway in bovine endometrial epithelial cells," (Feb. 2001) *Biol. Reprod.* 64(2):654-665.

Binelli, M. et al., "Interferon-τ modulates phorbol ester-induced production of prostaglandin and expression of cyclooxygenase-2 and phospholipase-A2 from bovine endometrial cells," (2000) *Biol. Repro.* 63:417-424.

Johnson, G.A. et al., "Interferon-tau and progesterone regulate ubiquitin cross-reactive protein expression in the ovine uterus," (Mar. 2000) *Biol. Reprod.* 62:622-627.

Johnson, G.A. et al., "Expression of the interferon tau inducible cross-reactive protein in the ovine uterus," (1999) *Biol. Reprod.* 61:312-318.

Johnson, G.A. et al., "Pregnancy and interferon-tau induce conjugation of bovine ubiquitin cross-reactive protein to cytosolic uterine proteins," (1998) *Biol. Reprod.* 58:898-904.

Johnson, G.A. et al., "Effects of the estrous cycle, pregnancy, and interferon tau on 2',5'-oligoadenylate synthetase expression in the ovine uterus," (May 2001) *Biology of Reproduction* 64:1392-1399.

Johnson, G.A. et al., "Development and characterization of immortalized ovine endometrial cell lines," (1999) *Biol. Repro.* 61:1324-1330.

Kiracofe, G.H. et al., "Pregnancy-specific protein B in serum of postpartum beef cows," (1993) *J. Anim. Sci.* 71:2199-2205.

Knight, E., Jr., "A 15-kDa interferon-induced protein is derived by COOH-terminal processing of a 17-kDa precursor," (1988) *J. Biol. Chem.* 263:4520-4522.

Korant, B.D. et al., "Interferon-induced proteins," (1984) *J. Biol. Chem.* 259(23):14835-14839.

Kozbor, D. and Roder, J.C., "The production of monoclonal antibodies from human lymphocytes," (1983) *Immunol. Today* 4(3):72-79.

Leung, S.T. et al., "Uterine lymphocyte distribution and interleukin expression during early pregnancy in cows," (2000) *J. Reproduction and Fertility* 119:25-33.

Loeb, K.R. "Conjugates of ubiquitin cross-reactive protein distribute in a cytoskeletal pattern," (1994) *Mol. and Cell. Biol.* 14(12):8408-8419.

Lowe J. et al., "Immunohistochemical localization of ubiquitin cross-reactive protein in human tissues," (1995) *J. Path.* 177:163-169.

Markusfeld, O. et al., "A routine 20-22 days post-service milk progesterone monitoring in dairy cows. Economic evaluation," (1990) *Br. Vet. J.* 146:504-508.

Mialon, M.M. et al., "Detection of pregnancy by radioimmunoassay of a pregnancy serum protein (PSP60) in cattle," (1994) *Reprod. Nutr. Dev.* 34(1):65-72.

Roberts, R.M. et al., "Glycoproteins of the aspartyl proteinase gene family secreted by the developing placenta," (1995) *Adv. Exp. Med. Biol.* 362:231-240.

Rueda, B.R. et al., "Recombinant interferon-τ regulates secretion of two bovine endometrial proteins," (1993) *J. Interferon Res.* 13:303-309.

Sasser, R.G. et al., "Detection of pregnancy by radioimmunoassay of a novel pregnancy-specific protein in serum of cows and a profile of serum concentrations during gestation," (1986) *Biol. Reprod.* 35(4):936-942.

Sasser, R.G. et al., "Detection of early pregnancy in domestic ruminants," (1987) *J. Reprod. Fert., Suppl.* 34:261-271.

Short, E.C. Jr. et al., "Expression of antiviral activity and induction of 2',5'-oligoadenylate synthetase by conceptus secretory proteins enriched in bovine trophoblast protein-1," (1991) *Biol. Repro.* 44:261-268.

Siddoo-Atwal, C. et al., "Elevation of interferon β-inducible proteins in ataxia telangiectasia cells," (1996) *Cancer Research* 56:443-447.

Spencer, T.E. et al., "Differential effects of intrauterine and subcutaneous administration of recombinant ovine interferon tau on the endometrium of cyclic ewes," (1999) *Biol. Reprod.* 61:464-470.

Spencer, T.E. et al., "Expression of interferon regulatory factors one and two in the ovine endometrium: effects of pregnancy and ovine interferon tau," (1998) *Biol. Reprod.* 58:1154-1162.

Sreenan and Diskin, Eds., "The extent and timing of embryonic mortality in the cow," (1986) *Embryonic Mortality in Farm Animals*, Martinus Niijhoff Publishers, pp. 1-11.

Staeheli, P. and Haller, O., "Interferon-induced human protein with homology to protein Mx of influenza virus-resistant mice," (1985) *Mol. Cell. Biol.* 4(8):2150-2153.

Staeheli, P. et al., "Polyclonal and monoclonal antibodies to the interferon-inducible protein Mx of influenza virus-resistant mice," *J. of Biol. Chem.* 260(3):1821-1825.

Staggs, K.L. et al., "Complex induction of bovine uterine proteins by interferon tau," (1992) *Biol. Reprod.* 59:293-297.

Stewart, H.J. et al., "Trophoblast interferons in early pregnancy of domestic ruminants," (1992) *J. Reprod. Fert. Suppl.* 45:59-68.

Szenci, O. et al., "Evaluation of false ultrasonographic diagnoses in cows by measuring plasma levels of bovine pregnancy-associated glycoprotein 1," (1998) *Vet. Rec.* 142(12):304-306.

Szenci, O. et al., "Comparison of ultrasonography, bovine pregnancy-specific protein B, and bovine pregnancy-associated glycoprotein 1 tests for pregnancy detection in dairy cows," (1998) *Theriogenology* 50:77-88.

Tanaka, K. et al., "The ligation systems for ubiquitin and ubiquitin-like proteins," (1998) *Mol. Cells* 8:503-512.

Teixeira, M.G. et al., "Bovine granulocyte chemotactice protein-2 is secreted by the endometrium in response to interferon-τ," (1997) *Endocrine* 6(1):31-37.

Thatcher, W.W. et al., "Uterine-conceptus interactions and reproductive failure in cattle," (Dec. 2001) *Theriogenology* 56:1435-1450.

Thatcher, W.W., et al., "New Strategies to Increase Pregnancy Rates," (1999) National Association of Animal Breeders Electronic Resource Guide.

Thatcher, W.W. et al., "Embryo health and mortality in sheep and cattle," (1994) *J. Anim. Sci.* 72(Suppl. 3):16-30.

Towbin, H. et al., "A whole blood immunoassay for the interferon-inducible human Mx protein," (1992) *J. Interferon Res.* 12(2):67-74.

Vallet, J.L. et al., "A low molecular weight endometrial secretory protein which is increased by ovine trophoblast protein-1 is a β2-microglobulin-like protein," (1991) *J. Endocrinology* 130:R1-R4.

Warnick, L.D. et al.,, "The relationship of the interval from breeding to uterine palpation for pregnancy diagnosis with calving outcomes in holstein cows," (1995) *Theriogenol.* 44:811-825.

Willard, J.M. et al., "Detection of fetal twins in sheep using a radioimmunoassay for PSPB," (1995) *J. Anim. Sci.* 73:960-966.

Willard, S.T. et al., "Early pregnancy detection and the hormonal characterization of embryonic-fetal motality in fallow deer," (1998) *Theriogenology* 49:861-869.

Xiao, C.W. et al., "Regulation of COX-2 and prostaglandin F synthase gene expression by steroid hormones and IFN-τ in bovine endometrial cells," (1998) *Endocrinol.* 139:2293-2299.

Xie, S. et al., "The diversity and evolutionary relationship of the pregnancy-associated glycoproteins, an aspartic proteinase subfamily consisting of many trophoblast-expressed genes," (1997) *Proc. Natl. Acad. Sci. USA* 94(24):12809-12816.

Xie, S. et al., "Identification of the major pregnancy-specific antigens of cattle and sheep as inactive members of the aspartic proteinase family," (1991) *Proc. Natl. Acad. Sci. USA* 88(22):10247-10251.

Yankey, S.J. et al., "Expression of the antiviral protein Mx in peripheral blood mononuclear cells of pregnant and bred, non-pregnant ewes," (Aug. 2001) *J. Endocrinology* 170:R7-R11.

Zoli, A.P. et al., "Radioimmunoassay of a bovine pregnancy-associated glycoprotein in serum: its application for pregnancy diagnosis," (1992) *Biol. Reprod.* 46(1):83-92.

Blomstrom, D.C. et al., "Molecular Characterization of the Interferon-induced 15-kDa Protein," (1986) *J. Biol. Chem.* 261:8811-8816.

Butler, J.E. et al., "Detection and partial characterization of two bovine pregnancy-specific proteins," (1982) *Biol. Reprod.* 26:925-933.

Charleston, B. and Stewart, H.J., "An interferon-induced Mx protein: cDNA sequence and high level expression in the endometrium of pregnant sheep," (1993) *Gene* 137:327-331.

Deutscher, G.H., "Estrous synchronization for beef cattle," U. Nebraska Cooperative Extension G85-741-A, 1993.

Dixit, V.D. et al. "Pregnancy stimulates secretion of adrenocorticotropin and nitric oxide from peripheral bovine lymphocytes," (Jan. 2001) *Biol. Repro.* 64:242-248.

Drew, M.I. et al., "Pregnancy determination by use of pregnancy-specific protein B radioimmunoassay in llamas," *JAVMA* 207(2):217-219.

Farrell, P.J. et al., "Accumulation of an mRNA and protein in interferon-treated Ehrlich ascites tumour cells," (1979) *Nature* 279:523-525.

Green, J. et al., "Pregnancy-associated bovine and obine glycoproteins exhibit spatially and temporally distinct expression patterns during pregnancy," (2000) *Biol. Reprod.* 62(6):1624-1631.

Hansen, T.R. et al., "Transient ubiquitin cross-reactive protein gene expression is the bovine endometrium," (1997) *Endocrinoogy* 138(11):5079-5082.

Hirako, M. and Takahashi, H., "Oestrone sulfate commences and increase around 50 days of gestation in bovine peripheral blood," (2000) *Reprod. Fertil. Dev.* 12(7-8):351-354.

Holdsworth, R.J. et al., "A rapid direct radioimmunoassay for the measurement of oestrone sulphate in the milk of dairy cows and its use in pregnancy diagnosis," (1982) *J. Endocrin.* 95:7-12.

Horisberger, M.A. and Hochkeppel, H.K., "An interferon-induced mouse protein involved in the mechanism of resistance to influenza viruses," (1985) *J. Biol. Chem.* 260(3):1730-1733.

Humblot, P. et al., "Pregnancy-specific protein B, progesterone concentrations and embryonic mortality during early pregnancy in dairy cows," (1988) *Reprod. Fertil.* 83(1):215-223.

Imwalle, D.B. et al., "Effects of melengestrol acetate on onset of puberty follicular growth, and patterns of luteinizing homome secretion in beef heifers," (1998) *Biol. Reprod.* 58:1432-1436.

Mialon, M.M. et al., "Peripheral concentration of a 60-kDa pregnancy serum protein during gestation and after calving and in relationship to embryonic mortality in cattle." (1993) *Reprod. Nutr. Dev.* 33(3):269-282.

Moriyoshi, M. et al., "Early pregnancy diagnosis in the sow by saliva progesterone measurement using a bovine milk progesterone qualitative test EIA kit," (1996) *J. Vet. Med. Sci.* 58(8):737-741.

Morton, H. et al., "Immunosuppression detected in pregnant mice by rosette inhibition test," (1974) *Nature* 249:459-460.

O'Connor, M.L., http://www.inform.umd.edu/EdRes/Topic/AgrEnv/ndd/reproduc/ESTROUS SYNCHRONIZATION FOR THE LACTATING DAIRY HERD.html; http://www.das/psu.edu/reproduction/check/pdf/synchron.pdf; and http://www.ianr.unl.edu/pubs/beef/g741.htm, 1997.

O'Connor, M.L. "Estrous synchronization programs for the dairy herd," (1997) The Pennsylvania State University, College of Agricultural Sciences pp. 1-8.

Oltenacu et al., "Economic evaluation of pregnancy diagnosis in dairy cattle: a decision analysis approach," (1990) *J. Dairy Sci.* 73:2826-2831.

Ott, T.L. et al., "Effects of the estrous cycle and early pregnancy on uterine expression of Mx protein in sheep (*Ovis aries*)," (1998) *Biol. Reprod.* 49:784-794.

Patel, O.V. et al., "Effect of stage of gestation and foetal number on plasma concentration of a pregnancy serum protein (PSP-60) in cattle," (1998) *Res. Vet. Sci.* 65(3):195-199.

Perry, D.J. et al., "Cloning of interferon-stimulated gene 17: the promoter and nuclear proteins that regulate transcription," (1999) *Mol. Endocrin.* 13:1197-1206.

Potter, J.L. et al., "Precursor processing of pro-ISG15/UCRP, and interferon-beta-induced ubiquitin-like protein," (1999) *J. Biol. Chem.* 274:25061-25068.

Pru, J.K. et al., "Pregnancy and interferon-τ upregulate gene expression of members of the I-8 family in the bovine uterus," (Nov. 2001) *Biol. Reprod.* 65:1471-1480.

Pru, J.K. et al., "Production, purification, and carboxy-terminal sequencing of bioactive recombinant bovine interferon-stimulated gene product 17," (2000) *Biol. Reprod.* 63:619-628.

Pru, J.K., "Regulation of bovine uterine proteins and prostaglandin F2a release by interferon-τ," (2000) Ph.D. Thesis, University of Wyoming.

\* cited by examiner

SEQUENCE LISTING

```
<160> NUMBER OF SEQ ID NOS: 6

<210> SEQ ID NO 1
<211> LENGTH: 14
<212> TYPE: PRT
<213> ORGANISM: Artificial sequence
<220> FEATURE:
<223> OTHER INFORMATION: Synthetic peptide

<400> SEQUENCE: 1

Gln Arg Leu Ala His Leu Asp Ser Arg Glu Val Leu Gln Glu
1               5                   10

<210> SEQ ID NO 2
<211> LENGTH: 15
<212> TYPE: PRT
<213> ORGANISM: Artificial sequence
<220> FEATURE:
<223> OTHER INFORMATION: Synthetic peptide

<400> SEQUENCE: 2

Cys Gln Arg Leu Ala His Leu Asp Ser Arg Glu Val Leu Gln Glu
1               5                   10                  15

<210> SEQ ID NO 3
<211> LENGTH: 16
<212> TYPE: PRT
```

-continued

```
<213> ORGANISM: Artificial sequence
<220> FEATURE:
<223> OTHER INFORMATION: Synthetic peptide

<400> SEQUENCE: 3

Thr Val Ala Glu Leu Lys Gln Gln Val Cys Gln Lys Glu Arg Val Gln
1               5                   10                  15

<210> SEQ ID NO 4
<211> LENGTH: 17
<212> TYPE: PRT
<213> ORGANISM: Artificial sequence
<220> FEATURE:
<223> OTHER INFORMATION: Synthetic peptide

<400> SEQUENCE: 4

Cys Thr Val Ala Glu Leu Lys Gln Gln Val Cys Gln Lys Glu Arg Val
1               5                   10                  15

Gln

<210> SEQ ID NO 5
<211> LENGTH: 16
<212> TYPE: PRT
<213> ORGANISM: Artificial sequence
<220> FEATURE:
<223> OTHER INFORMATION: Synthetic peptide

<400> SEQUENCE: 5

Trp Leu Ser Phe Glu Gly Arg Pro Met Asp Asp Glu His Pro Leu Glu
1               5                   10                  15

<210> SEQ ID NO 6
<211> LENGTH: 17
<212> TYPE: PRT
<213> ORGANISM: Artificial sequence
<220> FEATURE:
<223> OTHER INFORMATION: Synthetic peptide

<400> SEQUENCE: 6

Cys Trp Leu Ser Phe Glu Gly Arg Pro Met Asp Asp Glu His Pro Leu
1               5                   10                  15

Glu
```

BOVINE PREGNANCY TEST

CROSS-REFERENCE TO RELATED APPLICATIONS

This application claims priority to U.S. Patent Application No. 60/325,663 filed Sep. 28, 2001, U.S. Patent Application No. 60/337,871 filed Nov. 8, 2001, U.S. Patent Application Nos. 60/377,987, 60/377,166, 60/380,043, 60/377,921, 60/377,165, 60/377,355, 60/377,829, and 60/380,042 filed May 2, 2002, all of which are incorporated herein by reference to the extent not inconsistent herewith.

BACKGROUND

There are over nine million dairy cows in the United States and Canada, and over twenty million worldwide. The dairy industry is a very competitive marketplace, and the pregnancy status of the herd is critical to maximizing profits. It is estimated that a non-pregnant cow costs the industry approximately five dollars per day. An accurate, rapid test for determining the pregnancy status of a herd would have a very important economic impact on ranch or farm operations and would increase milk production of the dairies, resulting in increased profitability for the dairies.

A number of antigens are known to be present in cows and sheep during pregnancy, and pregnancy has been evaluated by a variety of methods. Bovine Antigen Glycoprotein (U.S. Pat. No. 4,755,460, issued Jul. 5, 1988, and 4,895,804, issued Jan. 23, 1990) can be measured about 12-15 days after breeding. Early Pregnancy Factor (EPF) (U.S. Pat. No. 4,877,742, issued Oct. 31, 1989, and WO 00/51520, published Sep. 8, 2000) levels can be measured at about 20-40 days after breeding, such as with KEMS BioTest Ltd. (Littleton, Colo.) Animal Rapid Test for Bovine Pregnancy.

Interferon-tau is produced by bovine trophoblast tissue between days 15-24 of bovine gestation and prevents luteolysis by suppressing endometrial $PGF_{2\alpha}$ secretion. Interferon-tau induces or upregulates expression of a number of proteins in pregnant animals.

Proteins that are induced by IFN-τ include granulocyte chemotactic protein (GCP-2) (WO 94/12537, published Jun. 9, 1994 and Staggs, K. L. et al. [1998] "Complex Induction of Bovine Uterine Proteins by Interferon Tau" *Biol. Reprod.* 59:293-297), 2',5'-oligoadenylate synthetase (Short, E. C. et al. [2001] "Expression of antiviral activity and induction of 2',5'-oligoadenylate synthetase by conceptus secretory proteins enriched in bovine trophoblast protein-1" *Biol. Repro.* 44:261-268), β2-microglobulin (Vallet, J. L. et al. [1991] "A low molecular weight endometrial secretory protein which is increased by ovine trophoblast protein-1 is a β2-microglobulin-like protein," *J. Endocrinology* 130:R1-R4), IFN regulatory factors 1 (IRF-1) and 2 (IRF-2) (Spencer, et al. [1998] *Biol. Reprod.* 58:1154-1162; and Binelli M. et al. [2001] *Biol. Reprod.* 64(2):654-665), GCP-2 (Teixeira, M. G. et al. [1997] *Endocrine* 6:31-37); and 1-8U, 1-8D, and Leu-13/9-27 (Pru, J. K. et al. [2001] "Pregnancy and Interferon-τ Upregulate Gene Expression of Members of the I-8 Family in the Bovine Uterus" *Biol. Reprod.* 65:1471-1480; and Pru, J. K. [2000] "Regulation of bovine uterine proteins and prostaglandin F2a release by interferon-tau" Ph.D. Thesis, University of Wyoming). Leu-13 is the name of the protein encoded by the 9-27 gene. Cyclooxygenase-2 (COX-2) (Xiao, C W et al. [1998] "Regulation of COX-2 and prostaglandin F2a synthase gene expression by steroid hormones and IFN-τ in bovine endometrial cells," *Endocrinol.* 139:2293-2299 and Thatcher, W. W. et al. [2001] "Uterine-conceptus Interactions and Reproductive Failure in Cattle" *Theriogenology* 56:1435-1450) and PLA2 (Binelli, M. et al. [2000] "Interferon-tau modulates phorbol ester-induced production of prostaglandin and expression of cyclooxygenase-2 and phospholipase-A2 from bovine endometrial cells" *Biol. Repro.* 63:417-424) are also regulated by IFN-τ.

Teixeira, M. G. et al. (1997) "Bovine Granulocyte Chemotactic Protein-2 is Secreted by the Endometrium in Response to Interferon-tau," *Endocrine* 6(1):31-37 report that bovine 1-8 transcripts were detected on Days 15 and 18 of pregnancy and were absent on Day 12 of pregnancy and during the estrus cycle. Bovine 1-8 gene family members are not known to be secreted. This reference also reported that polyclonal antibodies to a GCP-2 peptide were generated in sheep, and used to demonstrate that GCP-2 is secreted by cultured endometrial cells, representing Day 14 of the estrus cycle, when dosed with IFN-τ.

Mx encodes a monomeric GTPase and is induced by IFN-τ (Ott, T. L. et al. [1998] "Effects of the Estrous Cycle and Early Pregnancy on Uterine Expression of Mx Protein in Sheep (Ovis aries)" *Biol. Reprod.* 59:784-794). In Ott et al. (1998), ovine Mx protein was detected using a monoclonal antibody directed against the amino terminus of human MxA (1319.35.126, supplied by M. Horisberger, Novartis, Basel Switzerland) and a Super ABC Mouse/Rat Kit (Biomeda, Foster City Calif.). U.S. Patent Applications No. 60/299,553 and 10/166,929 describe a method of determining pregnancy status of an animal by assaying the level of Mx and comparing it to the level of Mx in a non-pregnant animal. Mx protein was detected with ovine Mx peptide antiserum (#90618-2). Yankey, S. J. et al. (2001) "Expression of the antiviral protein Mx in peripheral blood mononuclear cells of pregnant and bred, non-pregnant ewes" *J. of Endocrinology* 170:R7-R11, describes the presence of Mx in peripheral blood mononuclear cells of pregnant ewes at Day 15 of pregnancy. Mx protein can also be used to detect viral infection (EP 0 725 081, published Aug. 7, 1996) using monoclonal antibodies to human Mx. Antibodies to human Mx and immunoassays for Mx have been described (Staeheli, P. and Haller, O. [1985] "Interferon-induced human protein with homology to protein Mx of Influenza virus-resistant mice" *Mol. Cell. Biol.* 5(8): 2150-2153; Towbin H. et al. [1992] "A Whole Blood Immunoassay for the Interferon-Inducible Human Mx Protein" *J. Interferon Res.* 12(2):67-74; U.S. Pat. No. 5,869,264, issued Feb. 9, 1999; 5,739,290, issued Apr. 14, 1998; and U.S. Pat. No. 6,180,102 issued Jan. 30, 2001). Antibodies to mouse Mx are described in Staeheli, P. et al. (1985) *Mol. Cell. Biol.* 5:2150-2153; Staeheli, P. et al. (1985) *J. Biol. Chem.* 260(3): 1821-1825; and Horisberger, M. A. et al. (1985) *J. Biol. Chem.* 260(3):1730-1733. One of the monoclonal antibodies in Towbin (1992) is reported to react with other species' Mx proteins (mouse, rat, bovine, and porcine), in addition to human Mx.

Another IFN-τ-induced protein is ubiquitin cross-reactive protein (UCRP), which was first identified in humans (Farrell, P. J. et al. [1979] *Nature* 279:523-525) and later characterized (Koran, B. D. [1984] "Interferon-induced Proteins" *J. Biol. Chem.* 259(23):14835-14839; Blomstrom, D. C. et al. [1986] *J. Biol. Chem.* 261:8811-8816; and Knight E. Jr. et al. [1988] *J. Biol. Chem.* 263:4520-4522). Human UCRP (hUCRP) and mouse UCRP encode proteins that are processed to 17 kDa but that migrate as 15 kDa on PAGE gels (Potter, J. L. et al. [1999] "Precursor processing of pro-ISG15/UCRP, an interferon-beta-induced ubiquitin-like protein" *J. Biol. Chem.* 274:25061-25068). These proteins are similar to ubiquitin, and are upregulated by interferon (IFN), hence they are also known as interferon-stimulated gene 15 (ISG15). ISG15 is involved in the viral response and in the recognition of pregnancy (Bebington, C. et al. [1999] "Localization of Ubiquitin and Ubiquitin Cross-Reactive Protein in Human and Baboon Endometrium and Decidua During the Menstrual Cycle and Early Pregnancy" *Biol. Reprod.* 60:920-928, and Bebington, C. et al. [1999] "Ubiquitin Cross-Reactive Protein Gene Expression is Increased in Decidualized Endometrial Stromal Cells at the Initiation of Pregnancy" *Molecular Human Reproduction* 5(10):966-972). Like ubiquitin, ISG15 becomes covalently attached to targeted intracellular proteins via a C-terminal LRGG amino acid sequence. Proteins that are coupled to ubiquitin often are degraded through the 26 S proteasome (Baboshina, O. V. [1996] "Novel multiubiquitin chain linkages catalyzed by the conjugating enzymes ESEPF and RAD6 are recognized by 26 S proteasome subunit 5," *J. Biol. Chem.* 271:2823-2831). Ubiquitin is conjugated to other proteins by E2-conjugating enzymes (Tanaka, K. et al. [1998] "The ligation systems for ubiquitin and ubiquitin-like proteins" *Mol. Cell.* 8:503-512).

The 17 kDa bovine analog of hUCRP (ISG15) was identified as bovine UCRP (bUCRP) or ISG17 (Austin, K. J. et al. [1996] "Ubiquitin Cross-Reactive Protein is Released by the Bovine Uterus in Response to Interferon During Early Pregnancy," *Biol. Reprod.* 54:600-606; Austin, K. J et al. [1996] "Complementary Deoxyribonucleic Acid Sequence Encoding bovine Ubiquitin Cross-Reactive Protein," *Endocrine* 5(2):191-197; and Perry, D. J. et al. [1999] "Cloning of Interferon-Stimulated Gene 17: The Promoter and Nuclear Proteins That Regulate Transcription," *Molecular Endocrinology* 13:1197-1206). ISG17 becomes covalently linked to targeted intracellular proteins, is released from endometrial cells, and may function as a paracrine modulator. Unlike ISG15, ISG17-conjugated proteins continue to accumulate rather than be degraded. Two of the 1-8 gene family members, bovine 1-8U and bovine Leu-13, have high homology with the E2-conjugating enzymes, and they retain critical amino acids for function. It has been suggested that they may function by conjugating ISG17 to proteins.

A normal bovine estrus cycle is about 21 days in length. ISG17 has been detected by Day 15 of pregnancy. It continues to increase to Day 17, and remains high through Day 26 (Hansen, T. R. et al. [1997] "Transient Ubiquitin Cross-Reactive Protein Gene Expression in the Bovine Endometrium," *Endocrinology* 138(11):5079-5082; and Spencer, T. E. et al. [1999] "Differential Effects of Intrauterine and Subcutaneous Administration of Recombinant Ovine Interferon Tau on the Endometrium of Cyclic Ewes," *Biol. Reprod.* 61:464-470). ISG17 was not detectable above background during the estrus cycle of non-pregnant bovine.

One ISG17 function is to become cross-linked to cellular proteins, as does ubiquitin. Conjugation of ISG17 to endometrial cytosolic proteins was observed by Western Blotting using a polyclonal antibody to an ISG17 polypeptide (Johnson, G. A. et al. [1998] "Pregnancy and Interferon-Tau Induce Conjugation of Bovine Ubiquitin Cross-Reactive Protein to Cytosolic Uterine Proteins," *Biol. Reprod.* 58:898-904). The peptide used to generate the polyclonal antibodies corresponds to amino acids 82 to 99 of ISG17. This polypeptide was chosen because it had a high antigenic index, 78% identity with ISG15, and low identity (22%) with ubiquitin. Attempts to use the antiserum to develop a pregnancy test met with limited or no success (Pru, J. K. [2000] "Regulation of bovine uterine proteins and prostaglandin F2a release by interferon-tau" Ph.D. Thesis, University of Wyoming, Appendix 1, page 1). Another antibody which has been utilized in the study of ISG17 is monoclonal antibody 5E9 (Pru, J. K. [2000] "Regulation of bovine uterine proteins and prostaglandin F2a release by interferon-tau" Ph.D. Thesis, University of Wyoming, Appendix 1).

The Johnson polyclonal antibody to ISG17 amino acids 82-89 was also used to study ISG17 induction by IFN-τ by Western blotting (Staggs, K. L. et al. [1998] "Complex Induction of Bovine Uterine Proteins by Interferon Tau," *Biol. Reprod.* 59:293-297).

ISG17 also can induce expression of IFN-τ in peripheral blood mononuclear cells (PMBCs) (Pru, J. K. et al. [2000] "Production, Purification, and Carboxy-Terminal Sequencing of Bioactive Recombinant Bovine Interferon-Stimulated Gene Product 17," *Biol. Reprod.* 63:619-628).

Ovine UCRP (oUCRP) has been cloned (Charleston, B. and Stewart, H. J. [1993] "An interferon-induced Mx protein: cDNA sequence and high level expression in the endometrium of pregnant sheep," *Gene* 137:327-331). Ovine UCRP is reported to be detectable by Day 13, and to remain high through Day 19 of ovine pregnancy (Johnson, G. A. et al. [1999] "Expression of the Interferon Tau Inducible Cross-Reactive Protein in the Ovine Uterus," *Biol. Reprod.* 61:312-318). Western blotting of oUCRP was performed using a polyclonal antibody to human UCRP.

Other factors, in addition to IFN-τ, may be responsible for the induction of UCRP (Johnson, G. A. et al. [2000] "Interferon-tau and Progesterone Regulate Ubiquitin Cross-Reactive Protein Expression in the Ovine Uterus," *Biol. Reprod.* 62:622-627).

Estrone sulfate was found to be increased around day 50 in bovine peripheral blood. (Hirako, M. and Takahashi, H. [2000], "Oestrone sulfate commences an increase around 50 days of gestation in bovine peripheral blood," *Reprod. Fertil. Dev.* 12(7-8):351-354.) Estrone sulfate analysis in urine or serum after Day 100 has also been used to confirm pregnancy (Holdsworth et al. [1982] *J. Endocrin.* 95:7-12 and Warnick et al. [1995] *Theriogenol.* 44:811-825).

PSP60 is disclosed in Mialon, M. M., et al. (1993), "Peripheral concentration of a 60-kDa pregnancy serum protein during gestation and after calving and in relationship to embryonic mortality in cattle," *Reprod. Nutr. Dev.* 33(3):269-82, to be present in peripheral blood from day 27 after artificial insemination until and beyond the end of pregnancy. Mialon, M. M., et al. (1994), "Detection of pregnancy by radioimmunoassay of a pregnancy serum protein (PSP60) in cattle," *Reprod. Nutr. Dev.* 34(1):65-72 discloses that testing 349 cows for PSP60 28, 35, 50 and 90 days post-insemination gave accurate results compared with other known tests. Patel, O. V., et al. (1998), "Effect of stage of gestation and foetal number on plasma concentration of a pregnancy serum protein (PSP-60) in cattle," *Res. Vet. Sci.* 65(3):195-199 discloses that PSP60 increased from day 20 post-oestrus to 20 days pre-partum.

Pregnancy-associated glycoprotein 1 (PAG-1) is disclosed in Xie, S., et al. (1991), "Identification of the major pregnancy-specific antigens of cattle and sheep as inactive members of the aspartic proteinase family," *Proc. Nat'l Acad. Sci. USA* 88(22):10247-10251. This article teaches that pregnancy in cattle and sheep can be diagnosed by the presence of this conceptus-derived antigen in maternal serum. Zoli, A. P., et al. (1992), "Radioimmunoassay of a bovine pregnancy-associated glycoprotein in serum: its application for pregnancy diagnosis," *Biol. Reprod.* 46(1):83-92 discloses a double-antibody radioimmunoassay for bovine PAG-1 which was detected in maternal peripheral blood beginning at day 22 of pregnancy and increasing progressively to day 270, and becoming undetectable by day 100 postpartum. Xie, S. et al. (1997), "The diversity and evolutionary relationship of the pregnancy-associated glycoproteins, an aspartic proteinase subfamily consisting of many trophoblast-expressed genes," *Proc. Nat'l Acad. Sci. USA* 94(24):12809-12816, teaches that cattle, sheep and probably all ruminant artiodactyla possess up to 100 or more pregnancy-associated glycoprotein genes, many of which are placentally expressed. Szenci, O. et al. (1998), "Evaluation of false ultrasonographic diagnoses in cows by measuring plasma levels of bovine pregnancy-associated glycoprotein 1," *Vet. Rec.* 142(12):304-306 taught that this antigen showed that before day 31 ultrasonographic scanning was not very sensitive because six of the 30 calving cows were incorrectly diagnosed as non-pregnant. 0.5 ng/ml was used as the cut-off point to determine pregnancy. Pregnancy Associated Glycoproteins (PAGs) can also be detected during early pregnancy (WO 99/47934, published Sep. 23, 1999). Szenci, O. et al. (1998) "Comparison of Ultrasonography, Bovine Pregnancy-Specific Protein B, and Bovine Pregnancy-Associated Glycoprotein 1 Tests for Pregnancy Detection in Dairy Cows" *Theriogenology* 50:77-88, describes a comparison of bovine pregnancy tests for days 26 to 58 after artificial insemination (AI). Green, J. et al. (2000), "Pregnancy-associated bovine and ovine glycoproteins exhibit spatially and temporally distinct expression patterns during pregnancy," *Biol. Reprod.* 62(6): 1624-1631, discloses that pregnancy-associated glycoproteins in sheep and cows are expressed in the trophectoderm or binucleate cells. Those expressed predominantly in bovine binucleate cells are expressed weakly if at all by day 25 placenta, but are present at the middle and end of pregnancy. Others, such as PAG-4, -5 and -9 are present at Day 25 and at earlier stages. Roberts, R. M., et al. (1995), "Glycoproteins of the aspartyl proteinase gene family secreted by the developing placenta," *Adv. Exp. Med. Biol.* 362:231-240, teaches that pregnancy in cattle and sheep can be diagnosed by the presence of placentally-derived antigens (pregnancy-associated glycoproteins or PAG-1) in maternal serum soon after implantation begins at about day 20 following conception.

Pregnancy-specific Protein B (PSPB) is disclosed in U.S. Pat. No. 4,554,256, issued Nov. 19, 1985; 4,705,748, issued Nov. 10, 1987; European Patent No. 0132750, published Feb. 13, 1985; and Sasser, R., et al. (1986), "Detection of pregnancy by radioimmunoassay of a novel pregnancy-specific protein in serum of cows and a profile of serum concentrations during gestation," *Biol. Reprod.* 35(4):936-942. Serum concentrations of PSPB exceeded 1 ng/ml by 30 days post-breeding and increased gradually through three months, six months, and nine months of gestation, declining steadily to less than 78 ng/ml by 21 days postpartum. PSPB could be measured in most cows by 24 days after breeding. Szenci, O. et al. (1998), "Comparison of ultrasonography, bovine pregnancy-specific protein B, and bovine pregnancy-associated glycoprotein 1 tests for pregnancy detection in dairy cows," *Theriogenology* 50(1):77-88, teaches that at days 26 to 58 after artificial insemination, pregnancy testing with PSPB diagnosed pregnant cows as accurately as measuring of PAG-1 or ultrasound; however, there were fewer false positive diagnoses with the PSPB test than the PAG-1 test. PSPB has also been tested in llamas (Drew, M. I. et al. [1995] "Pregnancy determination by use of pregnancy-specific protein B radioimmunoassay in llamas" *JAVMA* 207(2):217-219); deer (Willard, S. T. et al. [1998] "Early pregnancy detection and the hormonal characterization of embryonic-fetal mortality in fallow deer" *Theriogenology* 49:861-869); and sheep (Willard, J. M. et al. [1995] "Detection of fetal twins in sheep using a radioimmunoassay for PSPB" *J. Anim. Sci.* 73:960-966) for detection of twins. PSPB is also detectable after calving (Kiracofe, G. H. et al. [1993] "PSPB in serum of postpartum beef cows" *J. Anim. Sci.* 71:2199-2205). Polyclonal antibodies against PSPB are described in U.S. Pat. No. 4,705,748 and Humblot et al. (1988), "Pregnancy-specific protein B, progesterone concentrations and embryonic mortality during early pregnancy in dairy cows," *Reprod. Fertil.* 83(1):215-223.

Progesterone is an antigen which is present throughout pregnancy. Progesterone levels have been measured in milk or blood samples collected from cattle after 22-24 days, such as offered at Rocky Mountain Instrumental Laboratories Inc. (Fort Collins, Colo.), but measurements of progesterone in milk at days 18-22 yield unacceptably high rates of false positives (Oltenacu et al. [1990] *J. Dairy Sci.* 73:2826-2831 and Markusfeld et al. [1990] *Br. Vet. J.* 146:504-508). Moriyoshi, M. et al. (1996), "Early pregnancy diagnosis in the sow by saliva progesterone measurement using a bovine milk progesterone qualitative test EIA kit," *J. Vet. Med. Sci.* 58(8): 737-741 discloses that pregnancy could be diagnosed 17-24 days after last mating in sows. Polyclonal antibodies to progesterone are commercially available from many different sources including Research Diagnostics, Inc., Flanders, N.J., and are described in Humblot, F., et al. (1988) "Pregnancy-specific protein B., progesterone concentrations and embryonic mortality during early pregnancy in dairy cows," *Reprod. Fertil.* 83(1):215-223. Monoclonal antibodies to progesterone are available commercially through OEM Concepts, Tom's River, N.J.

Johnson, G. A. et al. (1998) "Pregnancy and Interferon-Tau Induce Conjugation of Bovine Ubiquitin Cross-Reactive Protein to Cytosolic Uterine Proteins," *Biol. Reprod.* 58:898-904, discloses polyclonal antibodies to ISG17. The peptide used to generate the polyclonal antibodies corresponds to amino acids 82 to 99 of ISG17, LVRNDKGRSSPYEVQLKQ. This polypeptide was chosen because it had a high antigenic index, 78% identity with ISG15, and low identity (22%) with ubiquitin. Attempts to use the antiserum to develop a pregnancy test met with limited or no success (Pru, J. K. [2000] "Regulation of bovine uterine proteins and prostaglandin F2a release by interferon-tau" Ph.D. Thesis, University of Wyoming, Appendix 1, page 1). Another antibody which has been utilized in the study of ISG17 is monoclonal antibody 5E9 (Pru, J. K. (2000) "Regulation of bovine uterine proteins and prostaglandin F2a release by interferon-tau" Ph.D. Thesis, University of Wyoming, Appendix 1). U.S. Patent Application 60/393,615 discloses cDNAs believed to be associated with early bovine pregnancy.

Prior bovine pregnancy tests have tested only single antigens. However, false positives may occur when single antigens are tested, since positive test results may occur for these antigens when certain viruses are present. Some antigens such as progesterone are present in lactating cows. Thus a test is needed which will reliably determine bovine pregnancy with minimal false positive results.

Methods of making assay devices are described in Millipore's Short Guide for Developing Immunochromatographic Test Strips (2nd ed). Other assay devices and methods are described in U.S. Pat. Nos. 4,313,734, 4,376,110, 4,435,504, 4,486,530, 4,703,017, 4,740,468, 4,855,240, 4,954,452, 5,028,535, 5,075,078, 5,137,808, 5,229,073, 5,591,645, 5,654,162, 5,798,273, and in EP 0810436A1, and WO 95/16207. Assay devices containing more than one test strip are described at the Unitec, Inc. website.

In cows, the estrus cycle is about 21 days. To determine when a cycling cow is ready for breeding, the cow can be observed for behavioral estrus. Alternatively, a cow can be induced or forced into estrus with effective hormone therapies. Estrus of an entire herd can be synchronized (U.S. Patent Nos. 3,892,855 issued Jul. 1, 1975, and 4,610,687 issued Sep.

9, 1986). Estrus synchronization, or preferably ovulation synchronization, is used in timed AI (TAI) breeding programs. TAI breeding programs involve precise estrus synchronization which allows for timed breeding without monitoring for behavioral estrus. Examples of methods for forcing estrus include U.S. Pat. No. 5,589,457 (issued Dec. 31, 1996), Ovsynch (Pharmacia Animal Health, Peapack, N.J.), Cosynch, Select Synch, Modified Select Synch, MGA/PGF, and Syncro-Mate-B. Such methods typically employ hormones such as prostaglandins, e.g. PGF2α (Lutalyse®, Pharmacia Upjohn, Peapack, N.J.; Bovilene®, Syntex; Animal Health, Des Moines, Iowa; and Estrumate® Haver Lockhart, Shawnee, Kans.), and gonadotropin-releasing hormone (GnRH). Ovsynch involves a GnRH injection followed by a prostaglandin injection one week later, followed by a second GnRH injection 48 hours later. Insemination is ideally then performed at 12-18 hours, preferably about 16 hours, after the second GnRH injection. Ovsynch is maximally effective when implemented between Days 18-20 of a 20-day bovine estrus cycle (Thatcher, W. W. et al. [2000] "New Strategies to Increase Pregnancy Rates" at the website nab-css.org/education/Thatcher.html Presynch (Pharmacia Animal Health, Peapack, N.J.) can be used to synchronize heifers before implementing Ovsynch. Presynch involves two prostaglandin injections. Some of the above-mentioned methods are also used on non-cycling cows to induce cycling, such as in lactating dairy cows. After precise estrus synchronization, animals need not be monitored for behavioral estrus and may be bred by appointment. Some animals may need estrus presynchronization before estrus synchronization. Melengestrol acetate (MGA™) in feed (Imwalle, D. B. et al. (1998) "Effects of melengestrol acetate on onset of puberty, follicular growth, and patterns of luteinizing hormone secretion in beef heifers" *Biol. Repro.* 58:1432-1436) or implants (U.S. Patent Publication No. 2001/0041697, published Nov. 15, 2001) can be used for presynchronizing estrus in heifers. Resynch is a program whereby animals are synchronized and bred, and then those animals that are determined to be open (not pregnant) are again synchronized and rebred.

Prostaglandin alone has been administered sequentially or simultaneously with artificial insemination to reduce the number of insemination administrations per herd required for achieving pregnancy (WO 02/04006, published Jan. 17, 2002).

Prostaglandin can be used as a single injection. An injection of about 2-5 cc of Lutalyse (prostaglandin PGF2α) will induce an animal with a mature corpus luteum to come into estrus in about 48-96 hours. Cattle typically have a functional corpus luteum during Days 5-18 of the cycle (Estrus Synchronization of Cattle, Publication F-3163, Oklahoma Cooperative Extension Service, Oklahoma State University). Animals induced into estrus can be bred at 2-5 days following a prostaglandin injection. Single injection prostaglandin programs are often used with estrus synchronization, corpus luteum palpation, or behavioral heat detection because only animals in certain stages of the estrus cycle will respond by going into estrus. Breeding by appointment with a standard prostaglandin program has not been recommended because the interval from injection to estrus varies depending on the stage of the cycle when prostaglandin is administered. For example, if a cow is at cycle Day 7-8 or Day 15-17, timed AI can be performed at about 72-80 hours after the injection (O'Connor, M. L. discussion found at the website inform.umd.edu/EdRes/Topic/AgrEnv/ndd/reproduce and das.psu.edu/reproduction/check/pdf/synchron.pdf). A risk of using prostaglandin injection for forcing estrus is that prostaglandin can cause abortion when given to pregnant animals. Estrus and ovulation synchronization allows cattle managers to concentrate heat detection efforts in a relatively short period of time or allows for TAI, which requires no heat detection (see the website ianr.unl.edu/beef/g741.htm).

There is a need in the art to determine pregnancy status during the breeding of livestock. In cattle, conception rates are low (Streenan and Diskin, Eds. [1986] Embryonic Mortality in Farm Animals, Martinus Nijhoff Publishers, 1-11) and spontaneous abortion rates are high, making pregnancy/non-pregnancy determination and rebreeding/inseminating important management tools. Particularly there is a need to determine pregnancy/non-pregnancy status during the estrus cycle in which insemination occurs or the first estrus cycle after insemination so that animals that are not pregnant can be most economically rebred. This need is particularly strong when raising livestock such as cattle, especially on dairy farms.

There is a need in the art for tests that determine pregnancy, and particularly non-pregnancy, status of animals during the estrus cycle in which insemination occurs or during the first estrus cycle after insemination. Knowing which animals are non-pregnant allows efforts to be directed towards forcing non-pregnant animals into estrus and/or watching for signs of estrus, in preparation for insemination, to decrease the time an animal is not pregnant. Pregnancy is dependent, not only on conception/fertilization but also on maternal recognition of pregnancy during the critical period, which allows for implantation. Up to 40% of total embryonic losses are estimated to occur between Days 8 and 17 of pregnancy in cattle (Thatcher, W. W. et al. [1994] "Embryo Health and Mortality in Sheep and Cattle," *J. Anim. Sci.* 72(Suppl. 3):16-30). In the absence of reliable pregnancy tests, the earliest time at which a non-pregnant animal can be identified is at the beginning of a new estrus cycle, by observation of behavioral estrus. Optimally, pregnancy/non-pregnancy status is determined towards the end of or after the critical period when pregnancy is maintained, Days 15-17 according to Binelli, M. et al. (2001) "Antiluteolytic Strategies to Improve Fertility in Cattle," *Theriogenology* 56:1451-1463, but before the end of the first estrus cycle, Days 18-20, allowing timed artificial insemination programs to be maximally effective. This reference discloses that pregnancy/non-pregnancy status is optimally determined during Days 17-18.

Additional technology relating to pregnancy testing in cows and other animals is disclosed in U.S. Provisional Patent Application Nos. 60/377,987, 60/377,166, 60/380,043, 60/377,921, 60/377,165, 60/377,355, 60/377,829, and 60/380,042, all filed May 2, 2002.

All references cited herein are incorporated herein by reference in their entirety to the extent that they are not inconsistent with the disclosure herein. Citation of the above documents is not intended as an admission that any of the foregoing is pertinent prior art. All statements as to the date or representation as to the contents of these documents is based on subjective characterization of the information available to the applicant, and does not constitute any admission as to the accuracy of the dates or contents of these documents.

SUMMARY OF THE INVENTION

This invention provides bovine pregnancy test methods and devices. The tests are also suitable for any animal producing the antigens tested for during pregnancy. Tests of this invention are suitable for testing pregnancy in ungulates and ruminant animals. Preferably, the tests are used for animals selected from the group consisting of cattle, sheep, goats, yak, water buffalo, bison, antelopes, gazelles, elk, reindeer, moose, bighorn sheep, swine, horses, giraffes, and camellids including bactrian and dromedary camels, llamas, alpacas, and vicunas. More preferably the animal is a cow. Preferably the pregnancy test is performed cowside, i.e., in the field or barn, without bringing the sample from the cow to a laboratory.

Three different groups of antigens (Antigen groups A, B and C) are present in whole blood during bovine pregnancy. Certain of these antigens are present in other fluids as well, such as serum, milk and urine. Group A is a combination of antigens present at highest levels approximately during days 15-30 post-conception. Group B is a combination of antigens generally present after approximately day 25 and generally remaining at a detectable level throughout pregnancy. Antigens of Group C are present throughout pregnancy.

The method comprises: testing a fluid derived from the animal for the presence of at least one Group A or Group B antigen; also testing the fluid for the presence of at least one Group C antigen; determining that the animal is pregnant if the test is positive for at least one Group A or Group B antigen and at least one Group C antigen; and determining that the animal is not pregnant if the test is negative for at least one Group C antigen.

Group A antigens are antigens present during early pregnancy and include interferon-tau induced proteins including Interferon-stimulated Gene 17 (ISG17; also known as "ubiquitin cross-reactive protein"), Mx, Granulocyte Chemotactic Protein (GCP-2), 2',5' oligoadenylate synthetase, B2-microglobulin, Interferon Regulatory Factors 1 and 2 (IRF-1 and IRF-2), and 1-8U, 1-8D, Leu-13/9-27 (also referred to as Leu-13), COX-2. Group A antigens also include Bovine Antigen Glycoprotein (BAG), Early Pregnancy Factor (EPF), Pregnancy Specific Protein B (PSPB), and Pregnancy Associated Glycoproteins 1, 4, 5 and 9 (PAG-1, PAG-4, PAG-5, and PAG-9).

The Group A, B, and C antigens are divisible into classes. Class 1 of each group comprises all antigens. Class 2 of each group comprises all antigens of Class 1 that are detectable in non-pregnant animals but are detectable at levels substantially above background levels in pregnant animals, such as Mx. Class 3 of each group comprises all antigens that are secreted and can be detected in bodily fluids, including ISG17. Class 4 of each group comprises all antigens that are detectable in whole blood. Class 5 of each group comprises all antigens of Class 4 that are detectable in plasma, such as ISG17. Class 6 of Group A comprises all antigens excluding Mx. Class 7 of each group comprises all antigens which are detectable only in pregnant animals, such as ISG17, 1-8U, and Leu-13/9-27. Class 1 of Group A includes, but is not limited to, ISG17, Mx, GCP-2,2', 5' oligoadenylate synthetase, 32-microglobulin, IRF-1, IRF-2, 1-8U, 1-8D, Leu-13/9-27, and COX-2. The methods and compositions of this invention are useful for testing Class 1, Class 2, Class 3, Class 4, Class 5, Class 6, and Class 7 antigens. IFN-τ antigens are a preferred class of Group A antigens.

Group B antigens are antigens present from approximately days 25 or 30 to 60 or more of pregnancy and include estrone sulfate, pregnancy serum protein 60 (PSP-60 pregnancy-associated glycoproteins 6 and 7 (PAG-6 and PAG-7), and pregnancy-specific protein B (PSP-B).

Group C antigens are antigens present during early, mid-, and late pregnancy and include progesterone.

This invention provides rapid multi-antigen, multi-functional commercial pregnancy test methods and devices that use at least one antigen selected from Group A or Group B, and also a Group C antigen. Preferably, at least one antigen from Groups A, B and C are used. The use of multiple antigens improves the accuracy and efficiency of the determination. The method of detection preferably utilizes standard immunochromatographic technology with visible colorimetric readout.

A positive result for the presence of antigens of Groups A and/or B and C in a fluid from the cow being tested indicates pregnancy with a high degree of accuracy. A negative result for the presence of antigen(s) of Groups A and/or B indicates non-pregnant status with a high degree of accuracy (whether or not antigen(s) from Group C are present). A positive result for antigens of Groups A and/or B and a negative result from antigens of Group C indicate non-pregnant status. Antigens from Groups A and B can be tested at the same time, and on the same test membrane (also referred to herein as "test strip"), or at different times and on different test membranes. Testing for Antigen C may also be done at the same time as Antigen A and/or B, and on the same test membrane, or at a different time on a different test membrane.

The assay devices of this invention may contain a single test membrane, or two or more test membranes. The test membranes may be present within a cassette, each receiving fluid from a single application, such as through an aperture in a test cassette equipped with means such as tubules for distributing said fluid to each test membrane. In one embodiment, the assay device contains two test strips, one for testing for the presence of antigens of Group A or B as described above, and one for testing for the presence of antigens of Group C. In another embodiment, the assay device contains three test strips, one for testing for the presence of antigens of Group A, one for testing for the presence of antigens of Group B, and one for testing for the presence of antigens of Group C. The test membranes may be arranged side by side or radiating out from a central point in a star-shaped arrangement.

This invention also provides kits which comprise one or more test membrane strips comprising binding partners for the antigens used in the assay method.

Assay devices of this invention may include cell lysing means such as detergents known to the art, or puncture or other physical means known to the art.

Preferred binding partners for Antigens A, B and C are antibodies specific thereto. They can be polyclonal or monoclonal antibodies. A first antibody may bind to the antigen to form a complex, and a second antibody may bind to the complex. Either the first or second antibody may be labeled, and either the first or second antibody may be immobilized on a substrate such as a test membrane for ease of detection.

This invention also provides a method for determining how long an animal has been pregnant, the method comprising: testing a fluid derived from the animal for the presence of Group A and Group B antigen; also testing said fluid for the presence of at least one Group C antigen; determining that the animal is not pregnant if the test is negative for at least one Group C antigen; determining that the animal is pregnant if the test is positive for at least one Group A or Group B antigen and at least one Group C antigen; and determining that the animal is in early pregnancy (for a cow 15-30 days) if the test is positive for at least one Group A antigen and at least one Group C antigen; determining that the animal is in mid- to late pregnancy (for a cow 30 days or more) if the test is positive for at least one Group B antigen and at least one Group C antigen; and determining that the animal is in mid-pregnancy (for a cow between about 30 and 60 days) if the test is positive for at least one Group A antigen, at least one Group B antigen and at least one Group C antigen.

This invention further provides a pregnancy assay comprising: (1) a cassette; (2) a test membrane housed within the cassette; (3) first antibodies specific to Group A or specific to Group B antigen, and first antibodies specific to Group C antigen, said first antibodies being capable of binding to the corresponding antigens to form first antibody-antigen complexes; (4) binding partners specific to each such complex; and (5) labels attached to said first antibodies or said binding partners. The binding partners capable of binding to the complexes may be second antibodies specific to said Group A or Group B antigen, and to said Group C antigen; or they may be second antibodies specific to each of the first antibodies. The binding partners may also be detection antigens capable of binding specifically to each of the first antibodies.

The binding partners for the complex, or the first antibodies, may be immobilized on a substrate such as a test membrane. The first antibodies or the binding partners for the complex may be labeled. Preferably, the labels used are detectably different for detecting each antigen. Immobilized antibodies or binding partners for the complexes may be laid down on the substrate in different patterns corresponding to whether they bind to Group A antigens or antibodies, Group B antigens or antibodies, or Group C antigens or antibodies.

The assay may be in the form of a cassette comprising all needed antibodies and antigens, or may be in the form of a kit which includes necessary antigens and/or antibodies or other reagents as separate reagents.

A preferred cassette comprises a sample aperture for introducing sample fluid into the assay, preferably with a sample pad positioned beneath the sample aperture. The cassette also comprises a substrate such as a test membrane for immobilizing antibodies and/or antigens. A filter may be positioned downstream from the sample aperture. The cassette also preferably comprises a test window positioned above the point on the test membrane wherein labeled first antibodies, labeled second antibodies, or labeled detection antigens are immobilized. The human eye or a detection device may be used to view test results through the test window.

The cassette may also comprise control antigens from Group A and/or Group B, and control Group C antigens. These may or may not be immobilized on the test membrane and may or may not be labeled. The cassette also preferably comprises binding partners for the control antigens. The binding partners may be labeled and may be immobilized on the test membrane. Preferably, the cassette also comprises a control window positioned above the test membrane at the point where the control antigens or their binding partners are immobilized, so that results can be viewed through the control window by the human eye or a detection device.

Methods of making assay devices of this invention are also provided, the methods comprising providing a test membrane; providing a housing for the test membrane; removably or fixedly placing on said test membrane labeled or unlabeled first antibodies specific to Group A or specific to Group B antigen, and labeled or unlabeled first antibodies specific to Group C antigen; removably or fixedly placing on said test membrane: labeled or unlabeled second antibodies specific to Group A or Group B antigen, and labeled or unlabeled second antibodies specific to Group C antigen; or labeled or unlabeled detection antigens capable of specifically binding to said first or second antibodies to Group A antigen, or labeled or unlabeled detection antigens capable of specifically binding to said first or second antibodies to Group B antigen, and labeled or unlabeled detection antigens capable of specifically binding to said first or second antibodies to Group C antigen; and placing the test membrane within said housing.

The method of making assay devices of this invention may also comprise: removably or fixedly placing on said test membrane control Group A or control Group B antigen and control Group C antigen; and removably or fixedly placing on said test membrane binding partners specific to said control Group A or control Group B antigen, and specific to said control Group C antigen.

The method may further comprise placing a sample pad and/or a filter within the housing.

The methods of this invention are preferably carried out using an immunological assay device as described above, but other testing methods known in the art for measuring antigens and antigen levels, either directly or indirectly, such as western blot, sandwich blot, ELISA, dot blot, slot blot, Northern blot, PCR, and antibody precipitation, are also useful in the methods of this invention.

In one embodiment of this invention, one membrane strip contains at least one antibody to at least one antigen of Group A, and at least one antibody to at least one antigen of Group B; and a second strip contains at least one antibody to at least one antigen of Group C. A positive result for the presence of antigens of Groups A, B and C in a fluid from the animal being tested indicates pregnancy with a high degree of accuracy. A negative result for the presence of antigen(s) of Groups A and B indicates non-pregnant status with a high degree of accuracy (whether or not antigen(s) from Group C are present). A positive result for antigens of Groups A and B and a negative result from antigens of Group C indicate non-pregnant status.

This invention also comprises methods of determining readiness of an ungulate or ruminant animal for breeding comprising determining that the animal is not pregnant using a pregnancy test of this invention, and watching for behavioral signs of estrus. If the animal is not pregnant, estrus can also be induced using art-known methods, followed by breeding of the animal.

DETAILED DESCRIPTION

Figure 1:
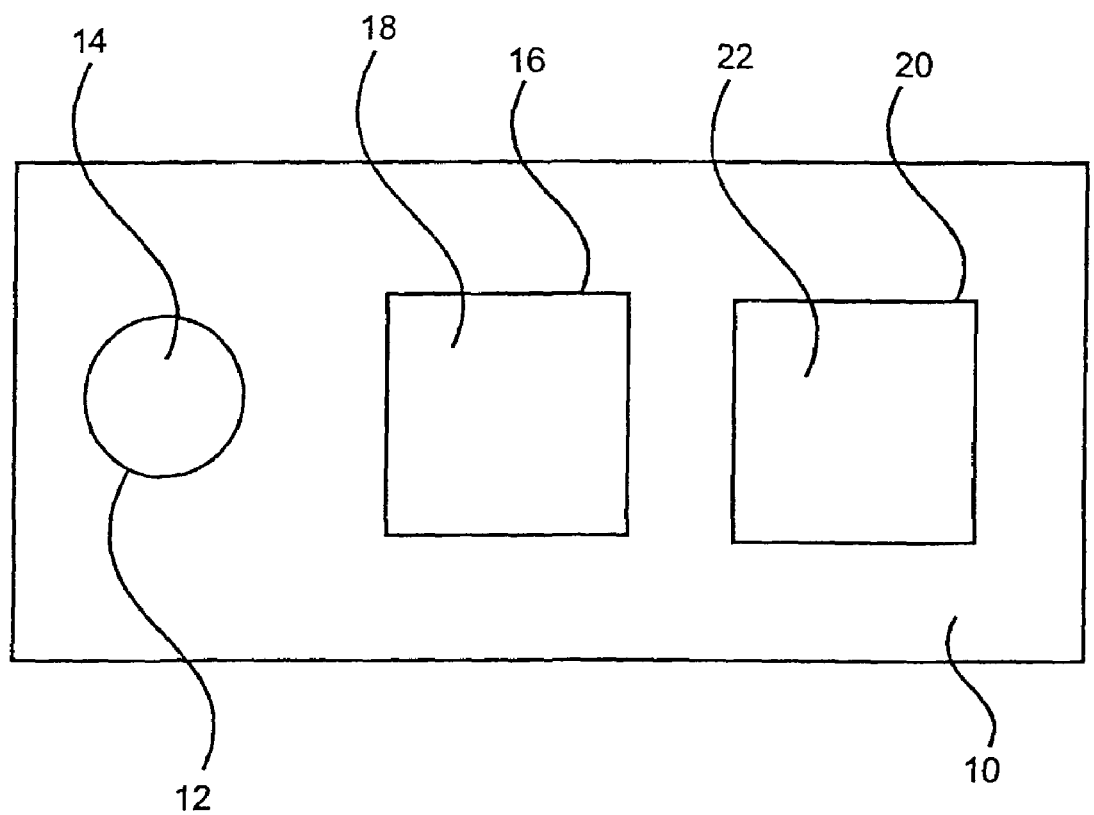
FIG. 1 is a top plan view of a test cassette of this invention.

This invention provides devices and methods for testing for pregnancy and non-pregnancy in ungulates and non-hoofed ruminates. The tests provided by this invention are especially useful during a time which coincides with the estrus cycle during which breeding occurs or the first estrus cycle after breeding of a non-pregnant animal. The tests provided by this invention are useful in estrus and ovulation synchronization programs, with pregnancy testing at a time allowing for resynchronization of non-pregnant animals within the first estrus cycle. The tests provided by this invention assay for the presence, absence, or particular level of selected Antigens A and/or B and C in a sample from a female animal. The tests of this invention are useful for testing cells, blood, plasma, serum, cells, milk, nasal secretions, ocular secretions, vaginal secretions, urine, and saliva samples. The tests provided by this invention are preferably immunoassays. Polyclonal and monoclonal antibodies are useful in such tests. Devices for performing such tests, methods of using such devices, and methods of making such devices are provided. Kits containing such devices are also provided. This invention provides a method for resynchronizing breeding with breeding cycle times of one estrus cycle or shorter. This invention also provides a method for breeding by forcing estrus and artificial insemination by appointment.

Animals suitable for the methods of this invention include ungulates and other ruminants. Ungulates that are ruminants include: cattle, sheep, goats, yak, water buffalo, and bison. Non-domesticated ungulates include: antelopes, gazelles, elk, reindeer, moose, bighorn sheep, giraffes, and other members of the cattle, sheep and goat families. Ruminant non-ungulates include: bactrian and dromedary camels and other camellids, such as llamas, alpacas, and vicunas. Ungulate non-ruminants include domesticated and non-domesticated swine and horses. Preferably the tests of this invention are useful for testing ungulates and non-hoofed ruminates, more preferably the tests of this invention are useful for testing ungulate and non-hoofed ruminate domesticated animals, and more preferably the tests of this invention are useful for testing bovine and ovine animals. The methods and devices of this invention are useful for any of the above-mentioned animals that can become pregnant. In bovines such animals are heifers, dairy cows, and beef cattle.

In general, immunobinding methods include obtaining a sample suspected of containing a protein, peptide, or antibody, and contacting the sample with an antibody or protein or peptide in accordance with the present invention, as the case may be, under conditions effective to allow the formation of immunocomplexes.

Conjugated as well as non-conjugated forms of the antigens may be detected using appropriate antibodies.

Contacting the chosen biological sample with the protein, peptide, or antibody under conditions effective and for a period of time sufficient to allow the formation of immune complexes (primary immune complexes) is generally a matter of simply adding the composition to the sample and incubating the mixture for a period of time long enough for the antibodies to form immune complexes with the proteins. During or after this time, the protein-antibody mixture may be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological, enzymatic tags, colloidal gold, or labels of standard use in the art. U.S. patents concerning the use of such labels include U.S. Pat. Nos. 5,360, 895; 3,817,837; 3,850,752; 3,939,350; 3,996,345; 4,277,437; 4,275,149; and 4,366,241. Of course, one may find additional advantages through the use of a secondary binding ligand such as a second antibody or a biotin/avidin ligand binding arrangement, as is known in the art.

The primary immune complexes may be detected by means of a second binding ligand that has binding affinity for the protein or the protein-specific first antibody. In these cases, the second binding ligand may be linked to a detection label. The second binding ligand is itself often an antibody, which may thus be termed "secondary" antibody. The primary immune complexes are contacted with the label, secondary binding ligand, or antibody, under conditions effective and for a period of time sufficient to allow the formation of secondary immune complexes. The secondary immune complexes may be coincidentally or later washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the desired protein or antibody specific thereto is used to form secondary immune complexes as described above. The second binding ligand contains an enzyme capable of processing a substrate to a detectable product and, hence, amplifying signal over time. After washing, the secondary immune complexes are contacted with substrate, permitting detection.

As a part of the practice of the present invention, the principles of an enzyme-linked immunoassay (ELISA) may be used. ELISA allows for substances to be passively adsorbed to solid supports such as plastic to enable facile handling under laboratory and field conditions.

In one embodiment, this invention comprises a "sandwich" ELISA, where antibodies to each desired antigen are immobilized onto a selected surface, such as a well in a polystyrene microtiter plate, cassette, or dipstick. Then, a test sample suspected of containing the selected antigen is contacted with the surface. After binding and optionally washing to remove non-specifically bound immunocomplexes, the bound antigen may be detected by a second antibody to the selected antigen.

Alternatively, polypeptides from the sample can be immobilized. Antibody competition may be used. Irrespective of the format used, ELISAs have certain features in common, such as coating (to prevent non-specific binding), incubating or binding, washing to remove non-specifically bound species, and detecting the immune complexes. It is common to use a secondary or tertiary detection means, rather than a direct procedure. Detection of the immune complex then requires a labeled secondary binding ligand or antibody, or a secondary binding ligand or antibody in conjugation with a labeled tertiary antibody or third binding ligand. The associated label may generate a color development upon contact with an appropriate chromogenic substrate.

A variant of ELISA is the enzyme-linked coagulation assay or ELCA (U.S. Pat. No. 4,668,621). In this system, the reactions can be performed at physiological pH in the presence of a wide variety of buffers.

Preferably, in the practice of this invention, the first antibody to a desired antigen is labeled with colloidal gold, the second antibody, which may be the same as the first, recognizing the same antigen, is immobilized. Washing occurs simultaneously with binding. Detection results from aggregation of gold. Colloidal gold is described at the website 2spi.com/catalog/chem./gold_labelling.html Immunoassay devices are known to the art and are made by companies such as Millipore and Arista and may be modified in accordance with the teachings hereof by one of ordinary skill in the art without undue experimentation.

As used herein, "cow" refers to female bovines, including heifers.

As used herein, "open" refers to an animal that is not pregnant.

As used herein, "cycling" refers to an animal that is experiencing an estrus cycle, i.e., is not pregnant.

As used herein, "breeding" refers to methods known in the art that pertain to making a female animal pregnant. Such methods include natural and artificial insemination. Breeding methods may include a waiting time after observation of behavioral estrus or after forcing estrus. In cattle, the waiting time after observing behavioral estrus is 12-18 hours. In cattle, after forcing estrus with prostaglandin on Day 17 or 18, the waiting time is 72-80 hours.

As used herein, "antibody specific to" refers to antibody that does not bind significantly to any sample components other than the desired component.

As used herein "binding partner" refers to a molecule that binds to an antigen, antibody, antibody/antigen complex or other molecule used in this invention. Preferred binding partners for antigens are antibodies specific to those antigens.

As used herein "immobilized on a test strip" or "fixedly placed on a test strip" with respect to a molecule means the molecule is attached to the test strip such that lateral flow of fluids across the test strip during an assay process will not dislodge the molecule. The term "removable" with respect to a molecule on a test strip means that the molecule is positioned on the test strip but not attached thereto, or attached so loosely as to be dislodged by fluid flow across the test strip during an assay and carried with the fluid.

As used herein, "pregnancy testing" refers to testing for pregnancy and/or non-pregnancy.

As used herein, "non-pregnancy" refers to the state of not being detectably pregnant.

As used herein, "early-stage bovine pregnancy" means to about day 25 or 30.

As used herein, "mid-stage bovine pregnancy" means about day 30 to about day 60.

As used herein, "late stage bovine pregnancy" means the period following mid-stage pregnancy.

As used herein, "whole blood" refers to blood as drawn. Whole blood contains a substantial amount of cells.

As used herein, "plasma" refers to blood with no substantial amount of cells. Plasma does contain clotting factors.

As used herein, "serum" refers to blood without a substantial amount of cells or clotting factors.

As used herein, "cowside" refers to an environment in which a domesticated animal is found, particularly in contrast to a laboratory environment.

As used herein, "breeding cycle time" refers to the time between one breeding of an animal and the next breeding during the next estrus cycle of the same animal.

As used herein, "normal background level" of an antigen refers to the level of a selected antigen in a non-pregnant animal in a control sample taken during a time in an animal's estrus cycle or after breeding corresponding to the time of taking a test sample.

Test devices of this invention may be in the form of cartridges, dipsticks, or other conformations known to the art. The test device may also be part of a kit which may contain instructions for use, instructions for comparison of test results with results of the same test done on non-pregnant animals, additional reagents, such as cells or fluids from non-pregnant animals, and other reagents known to the art.

Antibody supports and test membranes are also known to the art. In a preferred embodiment, the antibody supports are membranes to which the antibodies are removably, or fixedly attached. The sandwich assays provided by this invention may utilize polyclonal or monoclonal antibodies to the selected antigens. They may use the same or different polyclonal or monoclonal antibodies for capture and detection. The antibodies may be labeled using labels known to the art. Preferably, the label is colloidal gold. Preferably a sandwich assay is performed using an assay device such as a cartridge or a dipstick. Devices provided by this invention comprise detection and capture antibodies, support for the antibodies, a means for contacting the antibodies with a sample from an animal, a means of detecting binding of the antibodies to the selected antigens, and optionally, flow control elements to confirm that the sample is properly flowing within the test device. The devices may also contain means for measuring the level of the selected antigens relative to the amount of background level of the selected antigens. Some of the devices also contain means for lysing cells. Some of the devices also contain means for filtering serum or plasma from whole blood. When the selected antigen used as Antigen A is ISG17, the antibodies are preferably chosen from polyclonal antibodies anti-ISG17-4245, anti-ISG17-1000, and monoclonal antibody 5E9.

Preferred assay devices of this invention contain a sample window through which the sample is introduced into the assay device, and test and control windows where the test results are read. When the sample is placed in the sample window, a support absorbs liquid from the sample, and the liquid flows along the test membrane as a result of capillary action. The sample window and absorbent support provide means for contacting the antibodies with the sample. Detection antibody, previously removably placed on the support, is suspended in the sample liquid. If a selected antigen is substantially present in the sample liquid, the detection antibody will bind to it. As the sample liquid flows laterally down the support, the sample liquid passes capture antibodies, which have been immobilized on a support beneath the test window. If the selected antigen is substantially present, it will be bound to the detection antibody and will also bind to the capture antibody. The selected antigen may also bind to the capture antibody before being bound by the detection antibody. A sandwich of capture antibody, antigen, and detection antibody will be present under the test window. When the detection antibody has been labeled, e.g., with colloidal gold, a dark line of colloidal gold will appear in the test window as a result of the sandwich. As the liquid continues to flow past the capture antibody, whether or not a sandwich is formed, the liquid, which has picked up suspended control components such as control antigens, reaches control components such as antibodies immobilized in the control window. As the sample liquid passes by the immobilized control components, and antibody complexes are formed which are labeled, a dark line appears in the control window. Control antigens are removably placed on the support downstream or upstream of the capture antibodies but upstream of the area on the support where control capture antibodies are immobilized. If the control antigens are substantially different from the antigens to be tested they may be placed upstream of the capture antibodies, but if they are not substantially different, they must be placed downstream. The appearance of a dark line beneath the flow control window means that liquid is properly flowing. The test results are readable in about five minutes or less. The test results are read by observing the presence or absence of dark lines in the test and/or control windows. An absorbent pad may be used to enhance flow through the device by capillary attraction.

Antibodies to Antigens A, B and C are known to the art. Preferred polyclonal antibodies to Antigen A herein are polyclonal antibodies specific to ISG17, and more preferably are generated with, and capable of binding to, a polypeptide having an amino acid sequence selected from the group consisting of QRLAHLDSREVLQE (SEQ ID NO: 1), CQRLAHLDSREVLQE (SEQ ID NO: 2), TVAELKQQVCQKERVQ (SEQ ID NO: 3), CTVAELKQQVCQKERVQ (SEQ ID NO: 4), WLSFEGRPMDDEHPLE (SEQ ID NO: 5), and CWLSFEGRPMDDEHPLE (SEQ ID NO: 6). Other useful polyclonal antibodies are made using complete or partial amino acid sequences from ISG17, Mx, GCP-2,2',5' oligoadenylate synthetase, β2-microglobulin, IRF-1, IRF-2, 1-8U, 1-8D, Leu-13/9-27, COX-2, Bovine Antigen Glycoprotein, Early Pregnancy Factor, PAG-1, PAG-4, PAG-5, and PAG-9 of a mammal. Preferred polyclonal antibodies are anti-ISG17-4245, anti-ISG17-1000, specifically described herein below.

Useful polyclonal antibodies to B Antigens are made using complete or partial amino acid sequences from PSP-60, PAG-1, PAG-6, PAG-7, and PSPB. Useful polyclonal antibodies to C antigens are made using complete or partial amino acid sequences from progesterone.

Polyclonal antibodies can be prepared by immunizing an animal with a crude preparation of the desired antigen or a peptide fragment thereof, preferably a peptide fragment unique to that antigen. The animal is maintained under conditions whereby antibodies reactive with the desired antigen are produced. Blood is collected from the animal upon reaching a desired titer of antibodies. The serum containing the polyclonal antibodies (antisera) is separated from other blood components. The polyclonal antibody-containing serum can optionally be further separated into fractions of particular types of antibodies (e.g., IgG or IgM) or monospecific antibodies can be affinity purified from polyclonal antibody-containing serum.

Monoclonal antibodies to Antigens A, B and C are known to the art or may be prepared by methods known to the art. Preferred monoclonal antibodies to Antigen A herein are monoclonal antibodies specific to ISG17, and more preferably are generated with, and capable of binding to, a polypeptide having an amino acid sequence selected from the group consisting of QRLAHLDSREVLQE (SEQ ID NO: 1), CQRLAHLDSREVLQE (SEQ ID NO: 2), TVAELKQQVCQKERVQ (SEQ ID NO: 3), CTVAELKQQVCQKERVQ (SEQ ID NO: 4), WLSFEGRPMDDEHPLE (SEQ ID NO: 5), and CWLSFEGRPMDDEHPLE (SEQ ID NO: 6) and monoclonal antibodies made using complete or partial amino acid sequences from ISG17, Mx, GCP-2,2',5' oligoadenylate synthetase, β2-microglobulin, IRF-1, IRF-2, 1-8U, 1-8D, Leu-13/9-27, COX-2, Bovine Antigen Glycoprotein, Early Pregnancy Factor, PAG-1, PAG-4, PAG-5, and PAG-9 of a mammal. Preferred monoclonal antibodies are those made to the specific antigens described above. Monoclonal antibody 5E9 to ISG 17 described above may also be used.

Monoclonal antibodies useful in this invention may be obtained by well-known hybridoma methods. An animal is immunized with a preparation containing Antigens of type A, B or C or a peptide fragment thereof, preferably a peptide fragment unique to that antigen. A fused cell hybrid is then formed between antibody-producing cells from the immunized animal and an immortalizing cell such as a myeloma.

Monoclonal antibodies can be produced in large quantities by injecting antibody-producing hybridoma cells into the peritoneal cavity of mice and, after an appropriate time, harvesting ascites fluid from the mice, which yields a high titer of homogenous antibody. The monoclonal antibodies are isolated therefrom. Alternatively, the antibodies can be produced by culturing antibody-producing cells in vitro and isolating secreted monoclonal antibodies from the cell culture medium directly.

Another method of forming antibody-producing cells is by viral or oncogenic transformation. For example, a B-lymphocyte which produces an antibody specific to an antigen hereof may be infected and transformed with a virus, such as the Epstein-Barr virus, to give an immortal antibody-producing cell (Kozbon and Toder (1983) *Immunol. Today* 4:72-79).

Any indicator known to the art to detect antibody/protein binding may be used. Preferably, the indicator is labeled monoclonal or polyclonal antibodies which bind to the selected antigen, preferably labeled antibodies which bind to a substantially different epitope on the selected antigen from that to which the first antibodies bind. "Substantially different" in this context means that binding of the first antibody will not block binding of the second antibody, or vice versa. Labeled antibody/antigen complex may be viewed through a test window. Any label known to the art may be used for labeling the antibodies. The labeled antibody may be the first antibody to contact the antigen and form a complex, or the second antibody which contacts the antigen/first antibody complex to form a further complex. Preferably, the first or second antibody is immobilized on a substrate where the labeled complex can be viewed. A preferred label is colloidal gold, but any label known to the art may be used. The first and second antibodies may be polyclonal, monoclonal, or combinations thereof. In one embodiment, a first polyclonal antibody to Antigen A is anti-ISG17-4245, and the second antibody to Antigen A is anti-ISG17-1000 or the monoclonal antibody 5E9.

Some antigens, such as Mx, may be present in samples of non-pregnant animals at lower levels than in pregnant animals. Devices useful for testing for pregnancy using such proteins should include means for comparing the level of the selected antigen in the sample being tested with the level of the same antigen in a non-pregnant animal. Such comparison means include test supports comprising the same antibodies and labels which have previously been contacted with a sample from a non-pregnant animal. Such comparison means may also include a picture showing the appearance of such a test result from a non-pregnant animal. Such comparison means may also include the use of supports having a color identical to the color produced by testing a non-pregnant animal, so that such test results are not detectable by eye, and only a stronger color produced by testing a pregnant animal can be detected. Similarly, a filter having a color masking detection of binding produced by testing a non-pregnant animal, but allowing the stronger color of binding produced by testing a pregnant animal to be seen may be provided as such comparison means.

The tests of this invention may be performed with a sample containing any cell in which the selected antigen is found or in any bodily fluid in which the selected antigen is found. Preferably, the test does not substantially increase the risk of spontaneous abortion in a pregnant animal, as do tests involving removal of endometrial tissue. Cells, tissues, and fluids useful in the methods of this invention include whole blood, plasma, serum, urine, milk, nasal secretions, ocular secretions, vaginal secretions, and saliva, but blood, plasma, and serum are preferable.

Preferably the sample is a liquid, and the immunoassay test device is a lateral flow device comprising inlet means for flowing a liquid sample into contact with antibodies.

Kits are also provided comprising antibodies that bind immunologically to Antigens A and/or B and Antigen C, and a suitable container therefor. The kit may further comprise second antibodies that bind to the same Antigens (wherein the second antibodies bind a different epitope unless the detected antigen is a dimer or larger polymer). Preferably the first antibody is removably attached to a support and comprises a detectable label. The detectable label may be any label known in the art including but not limited to a fluorescent tag, a chemiluminescent tag, an enzyme, or colloidal gold. Preferably the label is colloidal gold. If the label is an enzyme, the kit may further preferably contain substrate for the enzyme.

The support may be any routinely used in immunological techniques. The container is preferably a polystyrene plate, cartridge, test tube, or dipstick. Preferably the second antibodies comprise detectable label. The kit may further comprise a buffer or diluent, and a suitable container therefor. As is known in the art, assays using immobilized detection antibodies may also be used. Other kit components, including reagent reservoirs, instructions, and the like are well known to those of skill in the art, and are contemplated for use in the kits described herein.

The tests of this invention are performed at a time after breeding when the presence of the selected antigens would indicate pregnancy. Depending on the animal, the sample should be obtained on a day selected from about Day 11 to about Day 15 to 20 after breeding (including any day in between). Preferably, particularly when the animal is a cow, the sample should be obtained from about Day 15 to Day 17 or Day 21 or Day 25 after breeding. Progesterone can be detected in cows in the first few days of pregnancy. Most preferably the sample should be obtained at Day 18 after breeding. ISG17 is detectable using the methods and compositions of this invention at about Day 11 until about Day 32 of pregnancy. The tests of this invention are preferably performed during the window of an estrus cycle in which methods for forcing estrus, such as by providing single injections of prostaglandin, are effective during that estrus cycle, but late enough in the cycle that the greatest number of naturally occurring spontaneous abortions will have occurred. Preferably in cows, the tests are performed at about Day 18. A single injection of prostaglandin, such as a Scc injection of prostaglandin PGF2α (Lutalyse, Pharmacia Upjohn, Peapack, N.J.), is effective for forcing estrus when a mature corpus luteum is available, such as during Day 17 of the bovine estrus cycle. In bovines, when Antigen A is ISG17, preferably the tests are performed during Days 14-32 after breeding, more preferably during Days 15-25, more preferably during Days 14-21, more preferably during Days 16-18, and most preferably during Day 18.

In methods of this invention for determining readiness for breeding and forcing estrus using the pregnancy assays provided herein, female animals are preferably presynchronized by any method known to the art including, but not limited to Presynch or MGA™. After presynchronization, animals are preferably synchronized by any method known to the art, including, but not limited to, Ovsynch, preferably in preparation for timed artificial insemination. Animals may be, but are preferably not, watched for behavioral estrus. Breeding may be performed by any method known to the art, but preferably, animals are bred by artificial insemination by appointment, at a time appropriate for the selected species and synchronization protocol. At a time appropriate for each species, about Day 18 in cattle, animals are tested for pregnancy using the devices and methods of this invention. Animals determined to be not pregnant are readied for breeding. Readying for breeding can involve waiting and watching for behavioral estrus, but preferably readying involves forcing estrus. Preferably readying for breeding by forcing estrus involves injecting prostaglandin, such as LUTALYSE® containing 25 mg of PGF2α. Forcing of more than one animal at once allows for synchronization of the animals. Estrus and preferably ovulation are forced, at an appropriate time for each species and forcing method, such as on about Day 18 in cattle, such that estrus and ovulation are synchronized to allow for AI by appointment, at 36-80 hours, preferably 72-80 hours, following prostaglandin injection. Animals may be bred by any method known in the art, but preferably by TAI. For the second time, at a time appropriate for each species, animals are tested for pregnancy using the compositions and methods of this invention. This cycle of breeding, pregnancy testing, forcing estrus and/or ovulation, and breeding, is continued until a satisfactory number of animals are determined to be pregnant. Practicing this cycle allows animals to be made pregnant in a minimum amount of time. The second round of breeding preferably occurs within or at the end of the timing of a normal estrus cycle.

The methods and devices of this invention are useful for testing for pregnancy in animals that are not infected by virus, or for testing for pregnancy in animals that are infected by virus when the selected antigen is not substantially induced by viral infection in the sample tested.

The methods and devices of this invention are preferably used for testing for pregnancy in animals that have not experienced spontaneous abortion within a previous period during which the selected antigens remain elevated over non-pregnant levels, e.g., the previous five days.

Two types of cows are artificially inseminated. The first type are naturally coming in and out of behavioral estrus, a phase which lasts about 12-18 hours, requiring intense observation by dairy farmers and breeders. If behavioral estrus is not observed and the cow is not artificially inseminated, the breeding window is missed and the cow will not return to estrus for about 21 days. The methods and compositions of this invention are useful to natural breeders. On Day 0 a cow in heat is observed. On Day 0, within 12-18 hours, the cow is artificially inseminated. On a day within Days 15-17 the methods and compositions of this invention are utilized to determine the pregnancy status of the cow. If the cow is determined to be non-pregnant (open), the breeder can wait until Day 21 and watch for behavioral estrus and artificially inseminate again, or give the cow an injection of prostaglandin and artificially inseminate again within 80 hours, thus keeping the cow in the same or first 21-day cycle.

The second type of artificially inseminated cow is a cow that is forced into estrus to be bred by appointment. This process is used by time breeders in synchronization programs. This process does not require a breeder to watch for behavioral estrus, because GnRH and prostaglandin are used to synchronize the estrus cycle and trigger ovulation. The methods and compositions of this invention are preferably utilized by these breeders. An example of the process begins with a presynchronizing injection of prostaglandin to ensure that the cow has a corpus luteum (about 18 days before artificial insemination (AI) is planned). After 14 days, an injection of GnRH is given to start a new follicle wave (about 10 days before AI). After 7 days, a second or breeding injection of prostaglandin is given (about three days before AI). The cow is then artificially inseminated on observation of behavioral estrus or on the morning of the third day following the breeding injection if behavioral estrus is not observed. At Day 17 after AI, the pregnancy status of the cow is determined, using the methods and compositions of this invention. Prostaglandin injections are given to cows determined to be not pregnant or open. These cows are then artificially inseminated again within 80 hours, which is within the 21-day window of the first estrus cycle. Using this process, the number of cows in a herd that are re-inseminated will increase about 50%.

The methods and compositions of this invention allow for reliable determination of pregnancy status early enough in the 21-day window that the cow can be resynchronized in time for the next estrus.

Visual signs of behavioral estrus (also called "standing heat") include riding of other cows, roughened hair or hair rubbed off on the tailhead indicating that the cow has been ridden by other animals, behavior such as following others, standing close and sniffing, nuzzling and licking another animal's back or rump. Cows in heat or near onset of heat tend to group together. They are generally more nervous than usual, and may bawl considerably, pace the fence and seem restless. Keen observers, familiar with their animals, often can tell cows in or approaching heat by subtle changes in normal appearance. A drop in milk production sometimes is observed. Another good indicator is stringy, clear (egg white appearance) mucus hanging from the vulvar opening or smeared on the tail or buttocks. Clear mucus discharges often can be seen in the gutter or on the ground where a cow had been resting. The vulvar lips will look moist and slightly swollen. A somewhat smoother surface is shown rather than the normal dry, finely wrinkled vulvar lips of a non-estrous cow. Further, the hairs of a cow in heat tend to be wet and matted and smeared by tail-rubbing activity. Bloody mucus, although not a consistent sign, can be observed between the second and fourth days following heat. This is not a sign of heat, but indicates the animal was in heat several days ago. Accurate detection may involve periods of observation of thirty minutes twice a day. Many devices to assist with heat detection are available on the market.

FIG. 1 shows a top plan view of a test cassette of this invention. The plastic case 10 housing the test strip used for the assay is perforated with a sample window 12 in which a sample may be dropped onto underlying sample pad 14. A further opening in the cassette, test window 16, allows the user to view capture area 18 of an underlying test membrane (also referred to herein as a "test strip") where capture antibodies have captured sample antigen/detection antibody complexes. The detection antibodies are labeled so as to be detectable through test window 16 when antigens to which they bind are present in the sample. These detection antibodies may be labeled with colloidal metals, colored latex particles, and/or other indicator compounds or conjugates known to the art which may be detected by eye or by detectors known to the art. A further control window 20 in the cassette allows the user to view control area 22 of an underlying test membrane area where capture antibodies have captured control antigen/detection antibody complexes.

Figure 2:
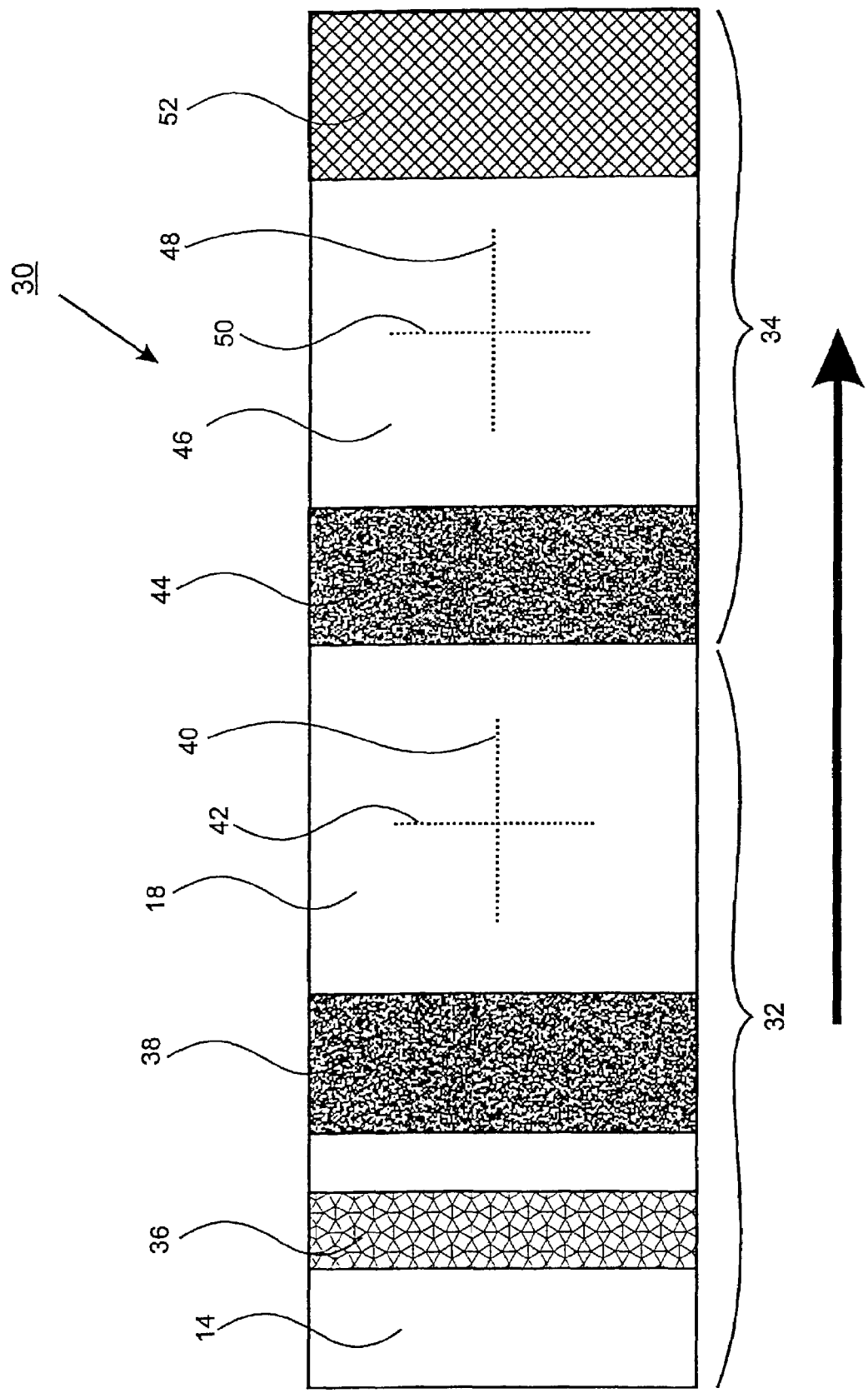
FIG. 2 is a view of a test strip for a two-antigen assay of this invention. Capture antibody lines are arranged in a "plus sign." The test strip may be housed within a test cassette as shown in FIG. 1.
Figure 3A:
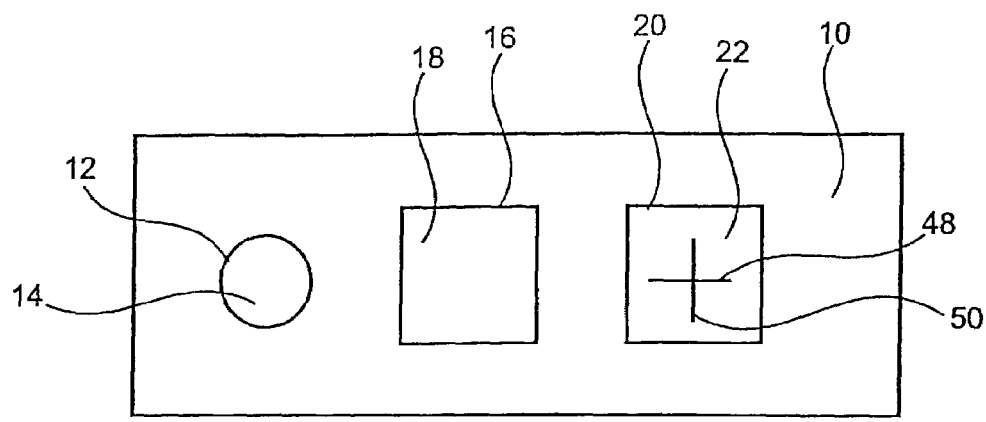
FIG. 3 (A-D) is a top plan view of test cassettes of this invention showing possible outcomes of the two-antigen assay performed on a test strip of FIG. 2.
Figure 3B:
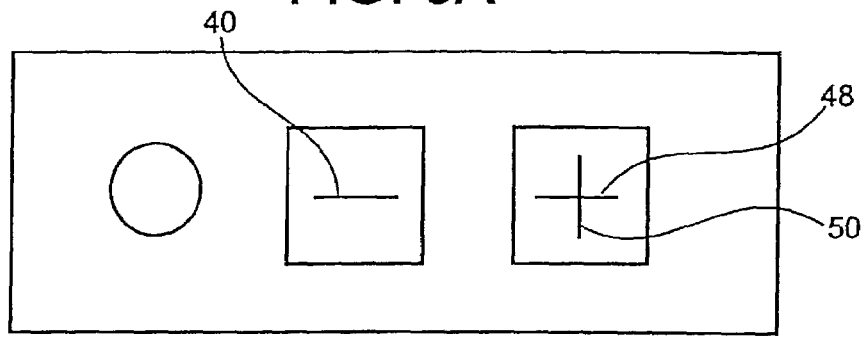
Figure 3C:
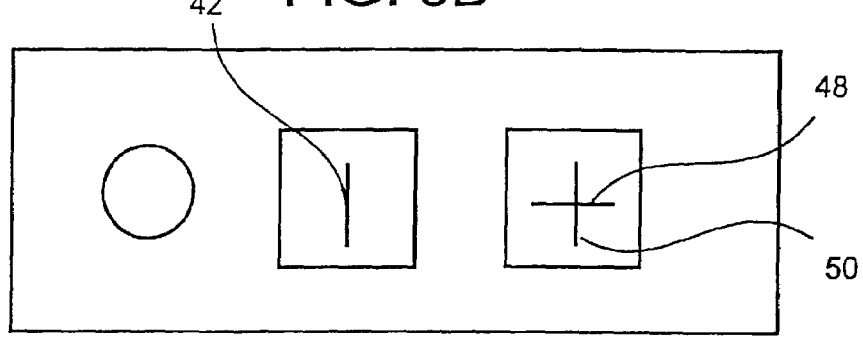
Figure 3D:
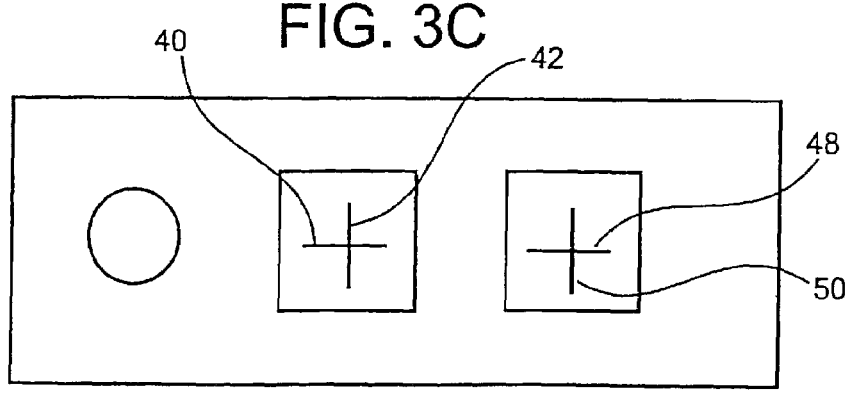

FIG. 2 shows test membrane 30 which comprises a test region 32 and a control region 34. Test region 32 comprises sample pad 14 onto which a sample fluid is dropped. Preferably a filter 36 is arranged next to sample pad 14 to separate contaminants from the sample, e.g., if the sample is blood, the filter would separate cells, debris, and other materials, allowing serum to flow farther down the test membrane. Next to filter 36 is detection antibody area 38 where detection antibodies, i.e., labeled antibodies that bind the antigen or antigens being tested for, are removably placed. These antibodies are unbound to the membrane or are so loosely bound as to be able to be carried along the test membrane in the direction of flow (large arrow) of the sample. As the sample fluid passes over detection antibody area 38, antigen(s) in the sample being tested become bound to their respective labeled antibodies. Next is capture area 18 in which capture antibodies to the antigen or antigens being tested for are fixedly bound. These capture antibodies bind and arrest the detection antibody/sample antigen complexes so that they are detectable through test window 16 of cassette 10 (FIG. 1). In a preferred embodiment, capture antibodies for a first antigen being tested (e.g., Antigen A) are laid down in a horizontal capture line 40, and capture antibodies for a second antigen being simultaneously tested (e.g., Antigen C) are laid down in a vertical capture line 42. As will readily be appreciated, alternatively, Antigen A could be laid down in a vertical line and Antigen C in a horizontal line.

In control region 34, control antigens are placed in control antigen area 44, unbound to test membrane 30, or so loosely bound as to be able to be carried along the test membrane in the direction of flow of the sample. As the sample fluid passes over control antigen area 44, control antigens (which are identical to the antigen(s) being tested for), are carried along and bound to detection antibodies in the fluid that have not been captured in capture area 18. Downstream from control antigen area 44 is control capture area 46 comprising capture antibodies, which are identical to the capture antibodies in the test region, bound to test membrane 30 and preferably laid down in the same pattern (e.g., control capture antibodies to Antigen A in horizontal control capture line 48 and antibodies to Antigen C in vertical control capture line 50). These control capture antibodies in control region 34 bind and arrest control antigen/detection antibody complexes so that they are detectable through control window 20 of cassette 10 (FIG. 1).

At the opposite end of test membrane 30 from sample pad 12 is an absorbent pad 52 to maintain fluid flow through the test membrane by capillary action.

FIG. 3 shows possible outcomes of an assay described above with respect to FIG. 2. In FIGS. 3A-3D, both horizontal control capture line 48 and vertical control capture line 50 are detected in control window 20, indicating that the test is working properly. In FIG. 3A, no labeled antibodies are detected in test window 16. This indicates neither antigen A or C were present in the sample. For a bovine pregnancy test in which capture antibodies for Antigen A were laid down in a horizontal line under test window 20 and capture antibodies for Antigen B were laid down in a vertical line under test window 20, this reading indicates the animal is not pregnant. In FIG. 3B, labeled antibodies for Antigen A are detected on horizontal capture line 40 beneath test window 16, but the vertical line (Antigen C) is not detectable. This indicates that the animal is not pregnant. In FIG. 3C, labeled antibodies are detected on the vertical line of test window 16 (for Antigen C), but are not detected on the horizontal line of test window 16 (for Antigen A). This indicates the animal is not pregnant, or is in late stage pregnancy. In FIG. 3D, horizontal and vertical lines 40 and 42 (Antigens A and C) are detected in the test window. This indicates that the animal is pregnant. As will be appreciated by those of skill in the art, if either the horizontal or vertical line is not visible in the control window, the test is flawed.

Figure 4:
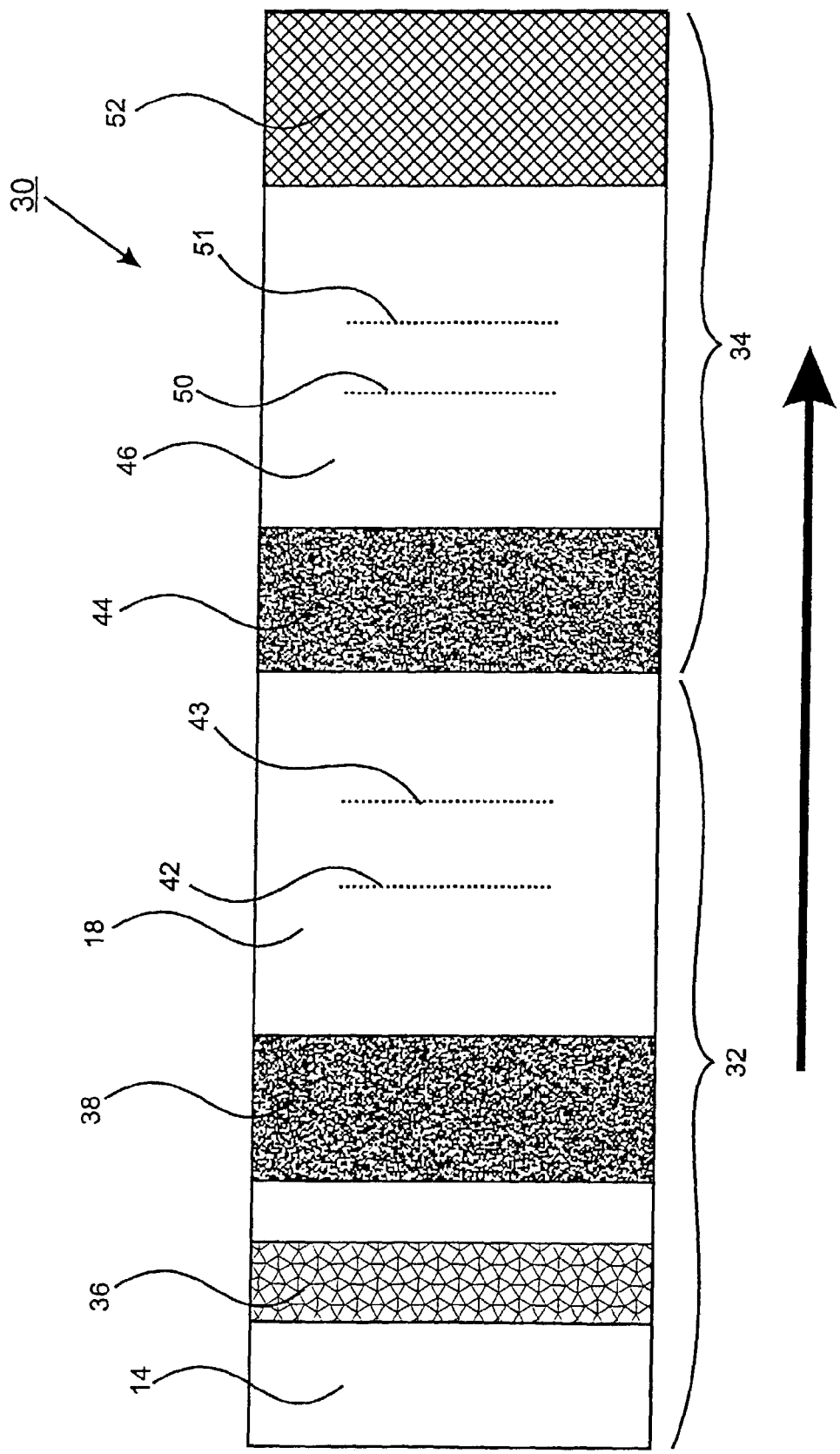
FIG. 4 is a view of an alternative test strip for a two-antigen assay of this invention. Capture antibody lines are arranged in parallel lines.

FIG. 4 shows a test membrane 30 like that of FIG. 2, but with the capture antibodies arranged in parallel vertical lines in both the test and control regions. As an illustration, for a preferred bovine pregnancy test of this invention, antibodies to Antigen A might be laid down in a first vertical capture line 42 while antibodies to Antigen C are laid down in a second vertical capture line 43 in capture area 18, and control Antigens A are laid down in a first vertical control capture line 50 and control Antigens C are laid down in a second vertical control capture line 51 in control capture area 46. The test is conducted as described above with respect to FIG. 2.

Figure 5A:
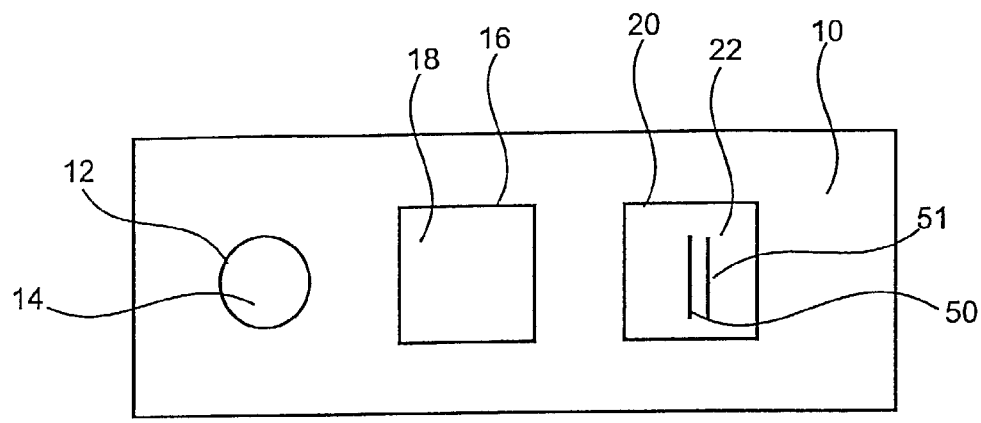
FIG. 5 (A-D) is a top plan view of test cassettes of this invention showing possible outcomes of the two-antigen assay performed on a test strip of FIG. 4.
Figure 5B:
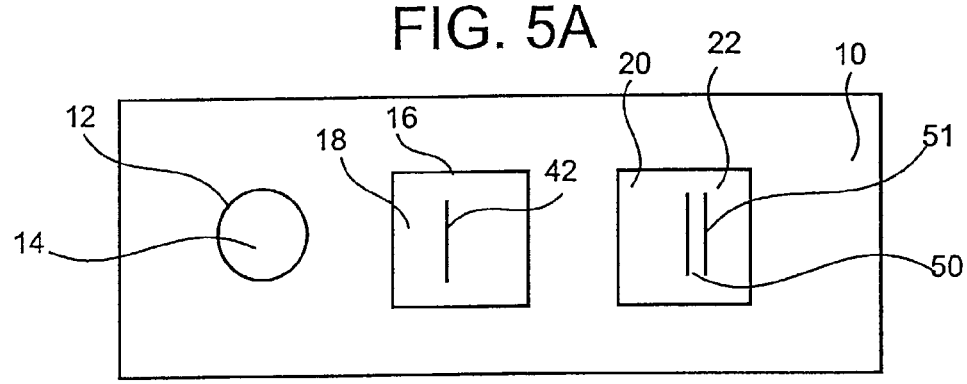
Figure 5C:
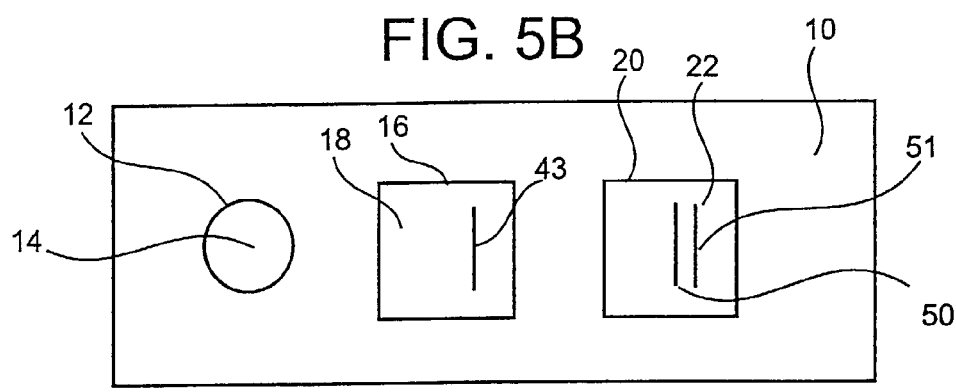
Figure 5D:
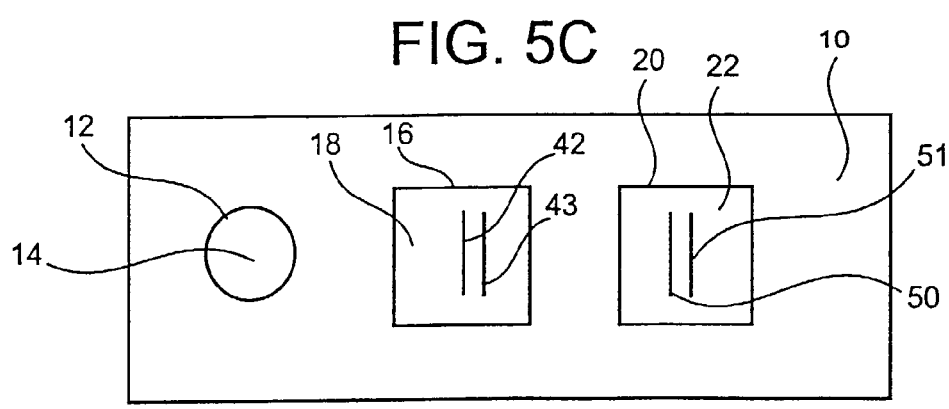

FIGS. 5A-5D are top plan views of test cassettes comprising plastic case 10 containing test membrane 30 as described for FIG. 4 showing possible outcomes of tests performed thereon. Again, both first and second vertical control capture lines 50 and 51 are shown as detectable under control window 20 of FIGS. 5A-5D, indicating that the test is functioning properly. If either line were missing under control window 20, this would indicate a defective test. In FIG. 5A, no vertical capture lines are detectable under test window 20. This indicates absence of both Antigens A and C in the sample, and that the animal is not pregnant. In FIG. 5B, vertical capture line 42 (antibodies to Antigen A) is shown as detectable under test window 20 and second vertical capture line 43 (antibodies to Antigen C) is not. In a bovine pregnancy test, this would indicate the animal is not pregnant. In FIG. 5C, vertical capture line 42 (indicating presence of Antigen A) is not detectable while the second vertical capture line 43 (indicating presence of Antigen C) is detectable. This indicates the animal is not pregnant or is in late stage pregnancy. In FIG. 5D, both first and second vertical capture lines 42 and 43 under test window 16 are detectable, indicating the presence of both Antigens A and C. The animal is therefore pregnant.

Figure 6A:
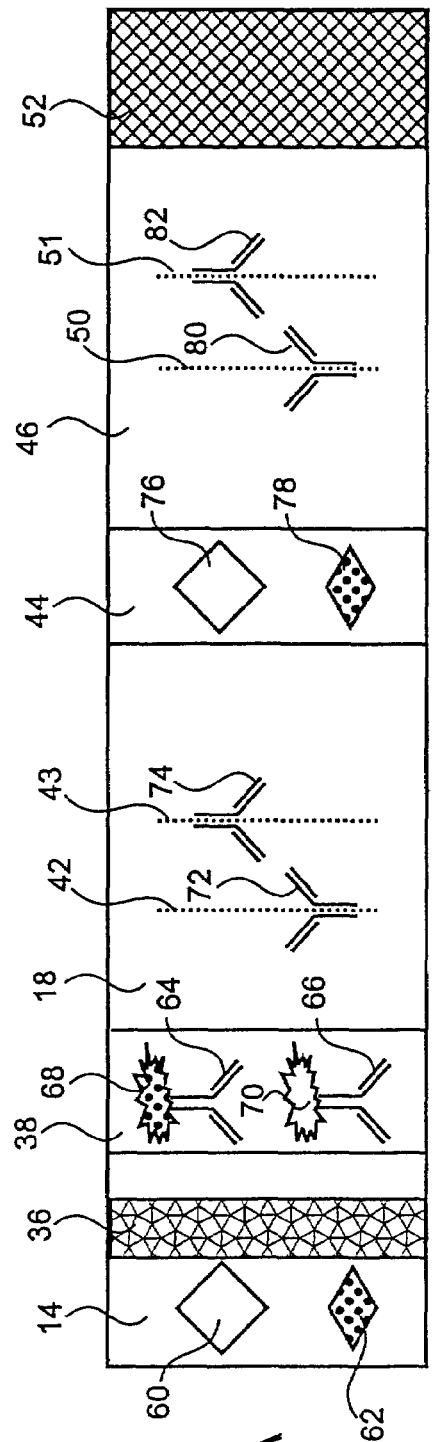
FIG. 6 is a schematic showing binding of antigens and antibodies at the sample Application, Capture and Detection stages respectively.
Figure 6B:
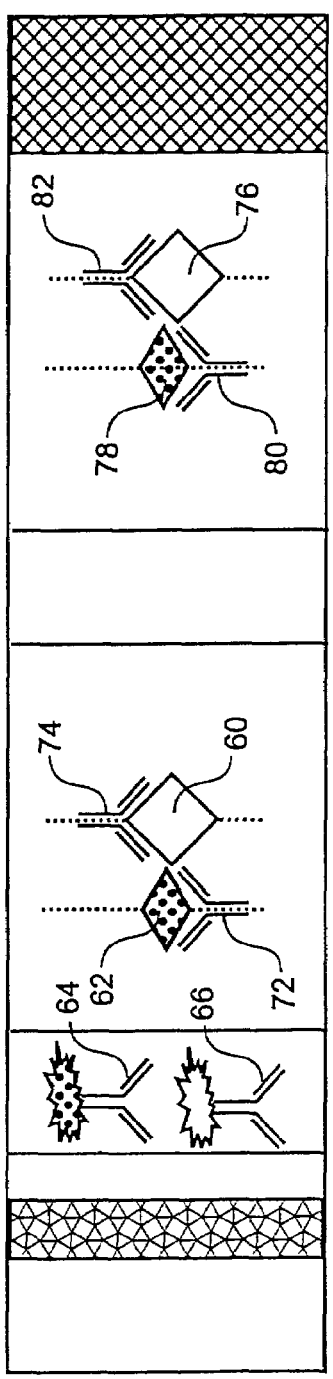
Figure 6C:
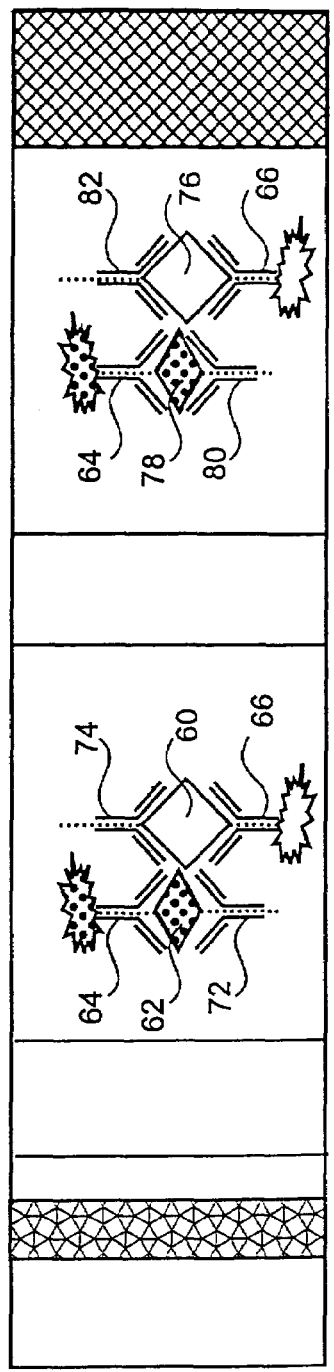

FIGS. 6A-6C show test membrane 30 as depicted in FIG. 4 with antigens and antibodies symbolically represented. In the top panel, FIG. 6A, the antigens are shown on sample pad 14 as they would be at the beginning of an assay (Application phase) when a sample containing both antigens A and C has just been applied through sample window 12 of a test cassette. For purposes of illustration, the open diamond 60 will be considered to represent Antigen C and the shaded diamond 62 to represent Antigen A. Detection Antibodies 64 and 66 are shown in detection antibody area 38. Detection antibodies to Antigen A 64 are shown labeled with a shaded label 68, and detection antibodies to Antigen C 66 are shown with an unshaded label 70. Unlabeled capture antibodies 72 and 74 are shown laid down in capture area 18 and bound to the test membrane in a pattern of two vertical capture lines 42 and 43 which lie directly beneath the test window of the cassette. Capture antibodies to Antigen A 72 are shown in first vertical capture line 42 (for purposes of illustration), and capture antibodies to Antigen C 74 are shown in second vertical capture line 43 (for purposes of illustration). Control antigens A 78 and control antigens C 76 are shown in control antigen area 44 and control capture antibodies to antigens A 80 and control capture antibodies to antigens C 82 are shown in control capture area 46 which lies directly beneath the control window of the test cassette. The same antibodies may be used for capture antibodies in capture area 18 and for control capture antibodies in control capture area 46.

In the middle panel, FIG. 6B, depicting the Capture phase of the test, Antigens A 62 and C 60 from the sample have moved from sample pad 14 to capture area 18 and been bound by capture antibodies 72 and 74 respectively. Control antigens A and C 78 and 76 have been swept up by the fluid moving across the test membrane and bound to control capture antibodies 80 and 82 respectively in control capture area 46.

In the lower panel, FIG. 6C, depicting the Detection stage of the test, detection antibodies A 64 and detection antibodies C 66 from the detection antibody area 38 are shown as having been swept along with the sample fluid, and bound with their respective antigens A 62 and antigens C 60, which are also bound with the respective capture antibodies to antigen A 72 and capture antibodies to antigen C 74 in capture area 18. This lower panel also shows that detection antibodies 64 and 66 have bound with their respective control antigens 76 and 78 and control capture antibodies 80 and 82 in control capture area 46. As will be appreciated by those of skill in the art, in practice, the binding of antigens with detection antibodies and capture antibodies occurs in any order, i.e., detection antibody/antigen complexes can also be present in the Capture phase of the test.

It will be appreciated by those of ordinary skill in the art that antibodies, devices, immunoassays, expression assays, detection methods, methods of making antibodies, and antigens other than those specifically disclosed herein are available in the art and can be employed in the practice of this invention. All art-known functional equivalents are intended to be encompassed within the scope of this invention.

The invention claimed is:

1. A pregnancy assay device for determining pregnancy or lack of pregnancy of a ruminant and/or ungulate animal, said assay device comprising:
   (a) a cassette; and
   (b) at least one test strip housed within said cassette;
   (c) first antibodies specific to a Group A antigen disposed in a horizontal or vertical line on said test strip, said first antibodies being selected from the group consisting of Interferon-stimulated Gene 17 (ISG17; Mx; Granulocyte Chemotactic Protein (GCP-2); 2',5' oligoadenylate synthetase; β2 microglobulin; Interferon Regulatory Factors 1 and 2; 1-8U; 1-8D; Leu-13/9-27; COX-2; Early Pregnancy Factor (EPF), Bovine Antigen Glycoprotein (BAG); Pregnancy Specific Protein B (PSPB) and Pregnancy Associated Glycoproteins 1, 4, 5 and 9 (PAG-1, PAG-4, PAG-5, and PAG-9); or
   first antibodies specific to a Group B antigen disposed in a horizontal or vertical line on said test strip, said first antibodies being selected from the group consisting of estrone sulfate, pregnancy serum protein 60 (PSP-60); pregnancy-associated glycoproteins 6 and 7 (PAG-6 and PAG-7), and pregnancy-specific protein B (PSP-B); and
   first antibodies specific to a Group C antigen disposed in a line on said test strip perpendicular and crossing the line of said first antibodies to a Group A or Group B antigen, said first antibodies to a Group C antigen being antibodies to progesterone;
   said first antibodies being capable of binding to the corresponding antigen to form first antibody-antigen complexes;
   (d) binding partners specific to each such complex on said test strip; and
   (e) labels attached to said binding partners;
   wherein detection of said labels forming a plus sign on said test strip indicating binding of Group A or Group B antibodies to Group A or Group B antigens and also binding of Group C antibodies to Group C antigens indicates the animal is pregnant; and failure to detect said labels indicating binding of Group C antibodies to Group C antigens indicates the animal is not pregnant.

2. The pregnancy assay device of claim 1 having a first and a second test strip, wherein said first test strip has thereon a first antibody specific to Group A antigen disposed in a horizontal or vertical line on said test strip and said second test strip has a first antibody specific to Group B antigen disposed in a horizontal or vertical line on said test strip, and wherein first antibodies specific to Group C antigen progesterone are disposed in vertical lines crossing horizontal lines formed by the first antibodies to Group A and Group B antigens, or said first antibodies specific to Group C antigen progesterone are disposed in horizontal lines crossing vertical lines formed by the first antibodies to Group A and Group B antigens, such that detection of said labels forming plus signs on said test strips indicating binding of Group A and Group B antibodies to Group A or Group B antigens and also binding of Group C antibodies to Group C antigens indicates the animal is pregnant; and failure to detect said labels indicating binding of Group C antibodies to Group C antigens indicates the animal is not pregnant.

3. The pregnancy assay device of claim 1 wherein said binding partners are second antibodies specific to each of said first antibodies.

4. The assay device of claim 1 wherein said cassette comprises a sample aperture for introducing sample fluid into said assay.

5. The assay device of claim 4 also comprising a sample pad positioned beneath said sample aperture.

6. The assay device of claim 4 also comprising a filter positioned downstream from said sample aperture.

7. The assay device of claim 1 wherein said cassette comprises at least one test window positioned above the point on said test strip where said plus sign is detectable.

8. The assay device of claim 1 also comprising control Group A and/or Group B antigens, and control Group C antigens on a test strip.

9. The assay device of claim 8 wherein said cassette also comprises at least one control window positioned above said test strip at the point where said control antigens are immobilized.

10. The assay device of claim 1 wherein said first antibodies specific to Group A or Group B antigen are disposed in a horizontal line and said first antibodies specific to Group C antigen are disposed in a vertical line on said test strip, whereby presence of the Group A or B antigens only in the sample causes detection of a minus sign, indicating the animal is not pregnant, and presence of Group A or B and Group C antigens in the sample causes detection of a plus sign, indicating the animal is pregnant.

11. An assay kit for determining pregnancy in a ruminant and/or ungulate animal, said kit comprising, in close association:

a) an assay device of claim 1;
b) instructions for use of said kit.

* * * * *